United States Patent
Laughlin et al.

(10) Patent No.: US 7,470,538 B2
(45) Date of Patent: Dec. 30, 2008

(54) CELL-BASED THERAPIES FOR ISCHEMIA

(75) Inventors: Mary J. Laughlin, Shaker Heights, OH (US); Stephen Haynesworth, Beachwood, OH (US); Vincent Pompili, Hudson, OH (US)

(73) Assignee: Case Western Reserve University, Cleveland, OH (US)

( * ) Notice: Subject to any disclaimer, the term of this patent is extended or adjusted under 35 U.S.C. 154(b) by 228 days.

(21) Appl. No.: 10/875,643

(22) Filed: Jun. 24, 2004

(65) Prior Publication Data

US 2005/0069527 A1 Mar. 31, 2005

Related U.S. Application Data

(63) Continuation-in-part of application No. 10/730,549, filed on Dec. 5, 2003.

(60) Provisional application No. 60/431,347, filed on Dec. 5, 2002.

(51) Int. Cl.
*C12N 5/00* (2006.01)
(52) U.S. Cl. .................... 435/325; 424/93.7
(58) Field of Classification Search ............ None
See application file for complete search history.

(56) References Cited

U.S. PATENT DOCUMENTS

| | | | |
|---|---|---|---|
| 4,670,467 A | 6/1987 | Hess et al. | |
| 5,486,359 A | 1/1996 | Caplan et al. | |
| 5,591,625 A | 1/1997 | Gerson et al. | |
| 5,612,211 A | 3/1997 | Wilson et al. | |
| 5,652,225 A | 7/1997 | Isner | |
| 5,654,186 A | 8/1997 | Cerami et al. | |
| 5,733,542 A | 3/1998 | Haynesworth et al. | |
| 5,840,693 A * | 11/1998 | Eriksson et al. ............ | 514/12 |
| 5,843,633 A | 12/1998 | Yin et al. | |
| 5,980,887 A | 11/1999 | Isner et al. | |
| 6,010,696 A | 1/2000 | Caplan et al. | |
| 6,387,367 B1 | 5/2002 | Davis-Sproul et al. | |
| 6,387,369 B1 | 5/2002 | Pittenger et al. | |
| 6,429,012 B1 | 8/2002 | Kraus et al. | |
| 6,461,645 B1 | 10/2002 | Boyse et al. | |
| 6,586,192 B1 | 7/2003 | Peschle et al. | |
| 6,676,937 B1 | 1/2004 | Isner et al. | |
| 2001/0051372 A1 | 12/2001 | Yin et al. | |
| 2002/0037278 A1 | 3/2002 | Ueno et al. | |
| 2002/0051762 A1 | 5/2002 | Rafii et al. | |
| 2002/0064519 A1 | 5/2002 | Bruder et al. | |
| 2002/0164794 A1 | 11/2002 | Wernet | |
| 2002/0168765 A1 | 11/2002 | Prockop et al. | |
| 2002/0197240 A1 | 12/2002 | Chiu | |
| 2003/0091547 A1 | 5/2003 | Edelberg et al. | |
| 2003/0148512 A1 | 8/2003 | Fanslow, III et al. | |
| 2003/0148952 A1 | 8/2003 | Crombreholme et al. | |
| 2003/0152558 A1 | 8/2003 | Luft et al. | |
| 2003/0180705 A1 | 9/2003 | Murohara et al. | |
| 2003/0199464 A1 | 10/2003 | Itescu | |
| 2003/0232050 A1 | 12/2003 | Isner et al. | |
| 2004/0131585 A1 | 7/2004 | Itescu | |

FOREIGN PATENT DOCUMENTS

| | | |
|---|---|---|
| WO | WO 89/03875 | 5/1989 |
| WO | WO 92/07573 | 5/1992 |
| WO | WO 93/13807 | 7/1993 |
| WO | WO 96/06933 | 3/1996 |
| WO | WO 97/12519 | 4/1997 |
| WO | WO 97/30083 | 8/1997 |
| WO | WO 99/37751 | 7/1999 |
| WO | WO 00/12683 | 3/2000 |
| WO | WO-01/93909 | 12/2001 |
| WO | WO 01/94420 | 12/2001 |
| WO | WO 03/078610 | 9/2003 |
| WO | WO-03/087333 | 10/2003 |
| WO | WO 03/095631 | 11/2003 |

OTHER PUBLICATIONS

Osman et al., "Cardiac Cell Transplantation: Closer to Bedside", Ann Thorac Surg 2003; 75: S674-7.
Minguell et al., "Biology and clinical utilization of mesenchymal progenitor cells", Braz J Med Biol Res, 2000, 33(3):881-887.
Minguell et al., "Mesenchymal Stem Cells", Exp Biol Med vol. 226(6):507-520.
Sukhikh et al., "Mesenchymal Stem Cells", Bulletin of Experimental Biology and Medicine, 2002, 133(2):103-109.
Fibbe et al., "Mesenchymal Stem Cells and Hematopoietic Stem Cell Transplantation", 2003, Ann. N.Y. Acad Sci, 996:235-244.
Vilkin et al., "Cell Transplantation for Post-Ischemic Heart Failure", Archives des Maladies du Coeur et des Vaisseaux, 2002, 95(12):1219-1225.
Itescu et al., "Myocardial Neovascularization by Adult Bone Marrow-Derived Angioblasts: Strategies for Improvement of Cardiomyocyte Function", Ann Hematol. 2002;81 Suppl 2:S21-S25.
Yang et al. Zhonghua Yi Xue Za Zhi, "Transplantation of cord blood endothelial progenitor cells ameliorates limb ischemia" 2003, 83(16) (Abstract).
Erices et al., "Human cord-blood-derived mesenchymal stem cells home and survive in the marrow of immunodeficient mice after systemic infusion", Cell Transplant, 2003, 12(6):555-61.

(Continued)

*Primary Examiner*—Lora E Barnhart
(74) *Attorney, Agent, or Firm*—Ropes & Gray LLP

(57) ABSTRACT

The invention provides, among other things, methods for treating an ischemic tissue in a subject in need thereof. The invention further provides methods for increasing the blood flow to an ischemic tissue in a subject in need thereof, such as to ischemic myocardium. The invention further provides cell-based formulations and related kits.

22 Claims, 20 Drawing Sheets

OTHER PUBLICATIONS

Rafii et al., "Therapeutic stem and progenitor cell transplantation for organ vascularization and regeneration", Nature Medicine, 2003, 9(3):702-712.

Anker et al., "Nonexpanded primary lung and bone marrow-derived mesenchymal cells promote the engraftment of umbilical cord blood-derived CD34(+) cells in NOS/SCID mice", Exp Hematol. 2003. 31(10).

Rodriguez-Manzaneque et al., "Thrombospondin-1 suppresses spontaneous tumor growth and inhibits activation of matrix metalloproteinase-9 and mobilization of vascular endothelial growth factor", PNAS, 2001, 98(22):12485-12490.

Wynter et al., CD34+AC133+ Cells Isolated from Cord Blood are Highly Enriched in Long-Term Culture-Initiating Cells, NOD/SCID-Repopulating Cells and Dendritic Cell Progenitors, Stem Cells, 1998, 16:387-396.

Burt et al., "Hematopoietic stem cell transplantation for cardiac and peripheral vascular disease", Bone Marrow Transplantation, 2003, 32:S29-S31.

Lazarus et al., "Human Bone Marrow-Derived Mesenchymal (Stomal) Progenitor Cells (MPCs) Cannot Be Recovered from Peripheral Blood Progenitor Cell Collections", Journal of Hematotherapy, 1997, 6:447-455.

Lazarus et al., "Ex vivo expansion and subsequent infusion of human bone marrow-derived stromal progenitor cells (mesenchymal progenitor cells): implications for therapeutic use", Bone Marrow Transplantation, 1995, 16:557-564.

Jaiswal et al., "Osteogenic Differentiation of Purified, Culture-Expanded Human Mesenchymal Stem Cells In Vitro", Journal of Cellular Biochemistry, 1997, 64:295-312.

Tateishi-Yuyama et al., "Therapeutic angiogenesis for patients with limb ischaemia by autologous transplantation of bone-marrow cells: a pilot study and a randomized controlled trial", The Lancet, 2002, 360:427-435.

Koc et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy", Journal of Clinical Oncology, 2000, 18(2):307-316.

Ankoma-Sey et al. (1998). "Coordinated induction of VEGF receptors in mesenchymal cell types during rat hepatic wound healing." Oncogene 17(1): 115-21.

Asahara et al. (1999). "Bone marrow origin of endothelial progenitor cells responsible for postnatal vasculogenesis in physiological and pathological neovascularization." Circ Res 85(3): 221-28.

Asahara et al.. (1999). "VEGF contributes to postnatal neovascularization by mobilizing bone marrow-derived endothelial progenitor cells." EMBO J 18(14): 3964-72.

Barry F et al. (2001). "The SH-3 and SH-4 antibodies recognize distinct epitopes on CD73 from human mesenchymal stem cells." Biochem Biophys Res Commun 289(2): 519-24.

Barry FP et al. (1999). "The monoclonal antibody SH-2, raised against human mesenchymal stem cells, recognizes an epitope on endoglin (CD105)." Biochem Biophys Res Commun 265(1): 134-9.

Chauhan A et al. (1996). "Aging-associated endothelial dysfunction in humans is reversed by L-arginine." J Am Coll Cardiol 28(7): 1796-1804.

Cheng T,. (2002). "Cell cycle entry of hematopoietic stem and progenitor cells controlled by distinct cyclin-dependent kinase inhibitors." Int J Hematol 75(5): 460-5.

D'Apuzzo et al. (1997). "The chemokine SDF-1, stromal cell-derived factor 1, attracts early stage B cell precursors via the chemokine receptor CXCR4." Eur J Immunol 27(7): 1788-93.

Fleming et al. (1998). "Monoclonal antibody against adult marrow-derived mesenchymal stem cells recognizes developing vasculature in embryonic human skin." Dev Dyn 212(1): 119-32.

Gehling et al. (2000). "In vitro differentiation of endothelial cells from AC133-positive progenitor cells." Blood 95(10): 3106-2.

Gill et al. (2001). "Vascular trauma induces rapid but transient mobilization of VEGFR2(+)AC133(+) endothelial precursor cells." Circ Res 88(2): 167-74.

Gu et al. (2000). "Association of extracellular matrix proteins fibulin-1 and fibulin-2 with fibronectin in bone marrow stroma." Br J Haematol 109(2): 305-13.

Hartlapp et al. (2001). "Fibrocytes induce an angiogenic phenotype in cultured endothelial cells and promote angiogenesis in vivo." FASEB J 15(12): 2215-24.

Haynesworth et al. (1996). "Cytokine expression by human marrow-derived mesenchymal progenitor cells in vitro: effects of dexamethasone and IL-1 alpha." J Cell Physiol 166(3): 585-92.

Haynesworth et al. (1992). "Characterization of cells with osteogenic potential from human marrow." Bone 13(1): 81-8.

Kalka et al. (2000). "Transplantation of ex vivo expanded endothelial progenitor cells for therapeutic neovascularization." Proc Natl Acad Sci U S A 97(7): 3422-7.

Kawamoto et al. (2001). "Therapeutic potential of ex vivo expanded endothelial progenitor cells for myocardial ischemia." Circulation 103: 634-637.

Klein et al. (1995). "Collagen type VI in the human bone marrow microenvironment: a strong cytoadhesive component." Blood 86(5): 1740-8.

Laughlin et al. (2001). "Hematopoietic engraftment and survival after unrelated donor umbilical cord blood (UCB) transplantation in adult recipients." New Engl J Med 344(24): 1815-22.

Mandel et al. (2001). "Isolation and Culture Expansion of Endothelial Progenitor Cells From UCB Using a Simple Selection Process." Blood 98(11): 55b (Abstract).

Ohta et al. (1998). "Suppression of hematopoietic activity in tenascin-C-deficient mice." Blood 91(11): 4074-83.

Pierelli et al. (2001). "CD105 (endoglin) expression on hematopoietic stem/progenitor cells." Leuk Lymphoma 42(6): 1195-206.

Ribatti et al. (1995). "Endogenous basic fibroblast growth factor is implicated in the vascularization of the chick embryo chorioallantoic membrane." Dev. Biol. 170: 39-49.

Rubinstein et al. (1998). "Outcomes among 562 recipients of placental-blood transplants from unrelated donors [see comments]." New England Journal of Medicine 339(22): 1565-1577.

Shi et al. (1999). "Evidence for circulating bone marrow-derived endothelial cells." Blood 92: 362-367.

Tschudi et al. (1996). "Effect of age on kinetics of nitric oxide release in rat aorta and pulmonary artery." J Clin Invest 98(4): 899-905.

Wang et al. (2002). "Receptor tyrosine kinase, EphB4 (HTK), accelerates differentiation of select human hematopoietic cells." Blood 99(8): 2740-7.

Zhang X et al. (2001). "Regulation of vascular endothelial growth factor by the Wnt and K-ras pathways in colonic neoplasia." Cancer Res 61(16): 6050-4.

Yin et a. (1997). "AC133, a Novel Marker for Human Hematopoietic Stem and Progenitor Cells." Blood 90(12):5002-12.

Buhring et al. "Expression of Novel Surface Antigens on Early Hematopoietic Cells." (1999) Ann NY Accad Sci 99 872:25-39.

Majka et al. "Expression, regulation and function of AC133, a putative cell surface marker of primitive human haematopoetic cells." (2000) Folia Histochem Cytobiol. 38:53-63.

Erices et al. "Mesenchymal progenitor cells in human umbilical cord blood." (2000) Br. J Haematol 109(1):235-42.

Strauer B et al. "Repair of Infarcted Mycocardium by Autologous Intracoronary Mononuclear Bone Marrow Cell Transplantation in Human." (2002) Circulation 1913-1918.

Assmus B et al. "Transplantation of Progenitor Cells and Regeneration Enhancement in Acute Myocardial Infarction (TOPCARE-AMI)." (2002) Circulation 106:3009-3017.

Amrani D et al. "Cardiovascular disease: potential impact of stem cell therapy." (2003) Expert Reu. Cardiovasc. Ther. 1(3), 453-461.

Hristov, M et al. "Endothelial Progenitor Cells." (2003) Arterioscler Thromb Vasc Biol. 1185-1189.

Stamm, C et al. "Autologous bone-marrow stem-cell transplantation for myocardial regeneration." (2003) The Lancet, vol. 361. 45-46.

Kawamoto, A et al. "Transplantation of endothelial progenitor cells for therapeutic neovascularization." (2002) Cardiovascular Radiation Medicine 3, 221-225.

Murohara, T et al. "Transplanted cord blood-derived endothelial precursor cells augment postnatal neovascularization." (2000) The Journal of Clinical Investigation vol. 105, No. 11, 1527-1536.

Rehman, J et al. "Peripheral Blood "Endothelial Progenitor Cells" Are Derived From Monocyte/Macrophages and Secrete Angiogenic Growth Factors." (2003) Circulation, 1164-1169.

Yang, C et al. "Enhancement of neovascularization with cord blood CD133+ cell-derived endothelial progenitor cell transplantation." (2003) Vascular Development and Vessel Remodeling, 1202-1212.

Goussetis, E. et al. "Kinetics of quiescent cord blood stem/progenitor cells with high proliferative potential in stem-cell expansion culture." 1: Cytotherapy, 2003; 5(6): 500-8.

Boxberger, O et al. "Mesenchymal stem cells can be differentiated into endothelial cells in vitro." 1: Stem Cells, 2004; 22(3):377-84.

Tuli, R et al. "Characterization of multipotential mesenchymal progenitor cell derived from human trabecular bone." 1: Stem Cells, 2003; 21(6):681-93.

Suva, D. et al. "Non-hematopoietic human bone marrow contains long-lasting, pluripotential mesenchymal stem cells." 1: J Cell Physiol. Jan. 2004; 198(1):110-8.

Kuwana, M. et al. "Human circulating CD14+ monocytes as a source of progenitors that exhibit mesenchymal cell differentiation." 1: J Leukoc Biol. Nov. 2003; 74(5):833-45 (Abstract only).

Covas, D.T. et al. "Isolation and culture of umbilical vein mesenchymal stem cells." 1: Braz J Med Biol Res. Sep. 2003; 26(9): 1179-83 (Abstract only).

Hao, S.G, et al. "Studies on the dynamics of biological characteristics of CD133+ cells from human umbilical cord blood during short-term culture." 1:Zhongguo Shi Yan Zue Ye Xue Za Zhi. Dec. 2003; 11(6):569-75 (Abstract only).

Chen, J et al. "Number of activity of endothelial progenitor cells from peripheral blood in patients with hypercholesterolemia." 1: Clin Sci (Lond). Apr. 20, 2004.

Burger et al. "Fibroblast growth factor receptor-1 is expressed by endothelial progenitor cells" *Blood*. 2002 15;100(10):3527-35.

Finney, et al, "Comparison of Umbilical Cord Blood Versus Bone Marrow-Derived Endothelial Precursor Cells in Mediating Neovascularization in a NOD/SCID Hind limb injury Model", (2002).

Finney, et al, "Umbilical Cord Blood versus Adult Bone Marrow-Derived Endothelial Precursor Cells (EPCs): In Vitro Characteristics and effectiveness in Vivo in Mediating Neovascularization after Femoral Artery Injury", Scientific Sessions. (2003).

Lodie, et al, "Systematic Analysis of Reportedly Distinct Populations of Multipotent Bone Marrow-Derived Stem Cells Reveals a Lack of Distinction", Tissue Engineering, vol. 8, No. 5, 739-751 (2002).

Schmeisser, et al, "Monocytes coexpress endothelial and macrophagocytic lineage markers and form cord-like structures in Matrigel® under angiogenic conditions", Cardiovascular Research, vol. 49, 671-680 (2001).

Ma Nan, et al, "Human cord blood cells induce and angiogenesis following myocardial infarction in NOD/scid-mice", Cardiovascular Research vol. 66 No. 1, 45-54 (2005).

Hristov, et al, "Endothelial progenitor cells: isolation and characterization", Trends in Cardiovascular Medicine, vol. 13, No. 5, 2001-2006, (2003).

Dragulescu, S. I., et al., "Protocol For Intracoronary Transplantation of Autologous AC133 Bone Marrow Stem Cells," TMJ, 54(1):14-18 (2004).

Peichev, M., et al., "Expression of VEGFR-2 and AC133 by circulating human CD34+ cells identifies a population of functional endothelial precursors," Blood, 95(3):952-958 (Feb. 1, 2000).

Haynesworth et al., "Cell Surface Antigens on Human Marrow-Derived Mesenchymal Cells Are Detected by Monoclonal Antibodies," Bone, 13:69-80, (1992).

Li et al., "Treatment of stroke in rat with intracarotid administration of marrow stromal cells," Neurology, 56:1666-1672, (2001).

Shake et al., "Mesenchymal Stem Cell Implantation in a Swine Myocardial Infarct Model: Engraftment and Functional Effects," Ann. Thorac. Surg., 73:1919-1926, (2002).

Zhao et al., "Human Bone Marrow Stem Cells Exhibit Neural Phenotypes and Ameliorate Neurological Deficits after Grafting into the Ischemic Brain of Rats," Experimental Neurology, 174:11-20, (2002).

"Plasticity of Adult Stem Cells," online, Medscape.com, retrieve from the internet: <URL:www.medscape.com/viewarticle/468360_12>, 2 pages, (2003).

Kocher et al., "Neovascularization of ischemic myocardium by human bone-marrow-derived angioblasts prevents cardiomyocyte apoptosis, reduces remodeling, and improves cardiac function," Natl Med, 7:430-436, (2001).

* cited by examiner

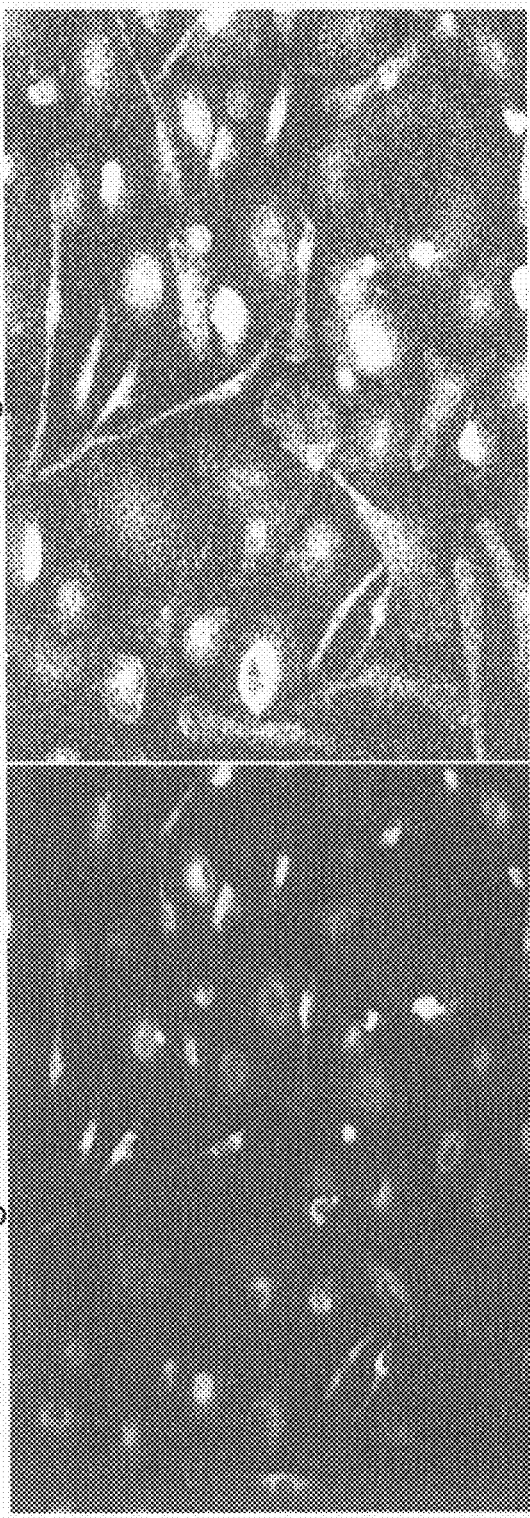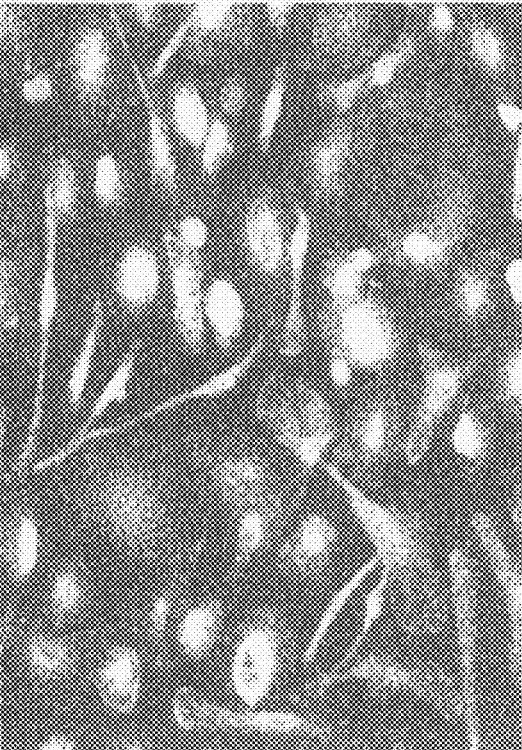

ISCHEMIC LEG - INJECTION OF CULTURE MEDIUM

ISCHEMIC LEG - INJECTION OF UCB-DERIVED EPC

Figure 15
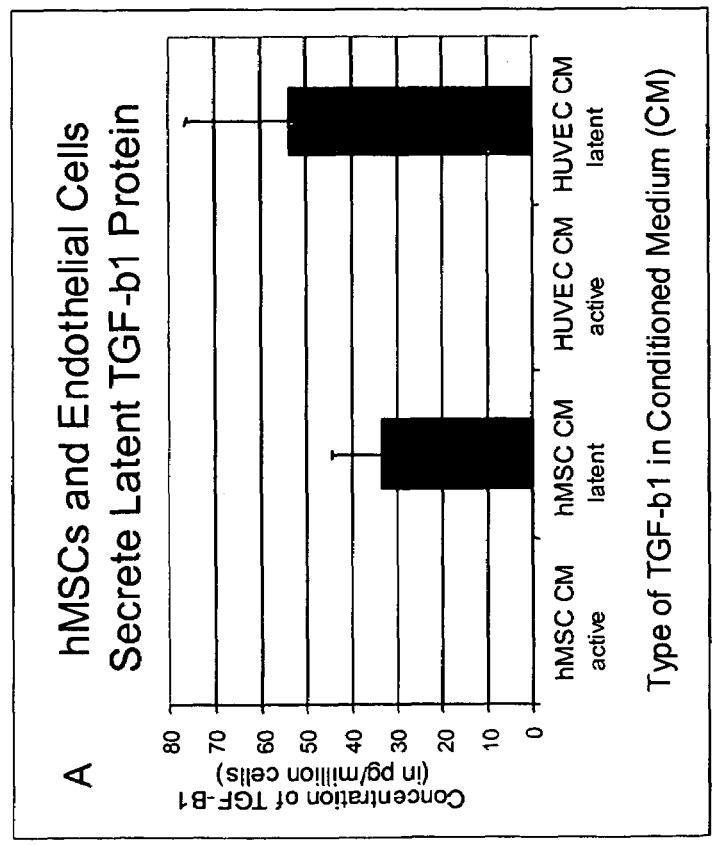
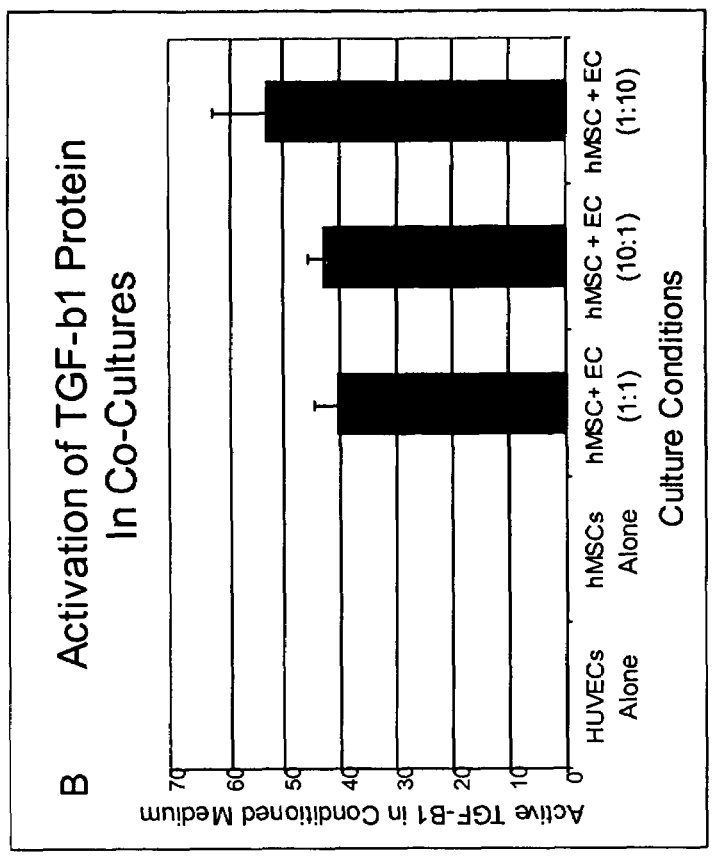

HUVECs IN VITROGEN 3D COLLAGEN GEL

DIL STAINED hMSCs 72 HOURS AFTER ADDITION TO HUVECs IN 3D COLLAGEN GEL

HUVECs ON 1% GELATIN COATED PLATE.

DIL STAINED hMSCs 1 HOUR AFTER ADDITION TO HUVECs IN 3D COLLAGEN GEL

CELL-BASED THERAPIES FOR ISCHEMIA

RELATED APPLICATIONS

This continuation-in-part application claims the benefit of the filing date of U.S. application Ser. No. 10/730549, filed Dec. 5, 2003, entitled "CELL-BASED THERAPIES FOR ISCHEMIA," which itself claims priority to U.S. Application No. 60/431,347, filed Dec. 5, 2002, entitled "VASCULAR ENDOTHELIAL PRECURSOR CELLS DERIVED FROM UMBILICAL CORD BLOOD." The entire teachings of both of these application are incorporated by reference herein.

GOVERNMENT SUPPORT

The invention described herein was supported, in whole or in part, by grant 1R21-HL-72362-01 from the National Institutes of Health. The United States government has certain rights in the invention.

BACKGROUND OF THE INVENTION

Atherosclerotic cardiovascular disease is a leading cause of morbidity and mortality in the industrialized western hemisphere. Coronary artery disease, the pathologic process of arterial luminal narrowing by atherosclerotic plaque resulting in obstruction of blood flow to the heart, accounts for about half of the deaths. Although catheter-based revascularization or surgery-based treatment approaches have been successful in restoring blood flow to ischemic myocardium in the majority of cases, the treatments are inadequate for a significant number of patients who remain incompletely revascularized. The ramifications of treatment limitations may be significant in patients who have large areas of ischemic, but viable myocardium jeopardized by the impaired perfusion supplied by vessels that are poor targets for conventional revascularization techniques. Treatment alternatives, including mechanical approaches such as percutaneous transluminal myocardial revascularization, and the like, have not produced encouraging results. Gene therapy using adenoviral vectors to augment cytokine production and, therefore, promote angiogenesis has shown promise, but this therapy has limitations and has not yet emerged as the optimal treatment for these patients. Therefore, therapeutic angiogenesis has attracted many researchers attempting to discover a way to circumvent the burden of chronic myocardial ischemia.

Atherosclerosis of the extremities is a leading cause of occlusive arterial disease of the extremities in patients over age 40. Peripheral vascular occlusive disease and its complications, including ulcers and even necrosis of the affected limb, is also common. Although percutaneous transluminal angioplasty and aorto-bifemoral bypass procedures are associated with acceptable morbidity and mortality risk and are usually initially successful, these interventions have not been shown to be effective long-term.

In an effort to provide treatment for myocardial ischemia and/or peripheral vascular occlusive disease, a number of angiogenesis techniques are now in clinical trial, including gene therapy and the use of growth factors such as vascular endothelial growth factor (VEGF) or basic fibroblast growth factor (bFGF) to induce or augment collateral blood vessel production. For optimal therapeutic outcome, these techniques rely on the availability of a resident population of mobilizable and hormone responsive vascular endothelial cells in the patient's circulation. However, an age-related diminution of vascular endothelial cell number and function has been observed in adults. In particular, in older patients who are most likely to suffer from vascular problems, both central (i.e. coronary) and peripheral, the number of hormone responsive endothelial cells is reduced and the number of dysfunctional endothelial cells is increased. Moreover, administration of cytokines to mobilize sufficient patient-derived responsive cells may worsen cardiovascular pathophysiology secondary to leukocytosis and/or activation of pro-coagulant processes.

Therefore, an alternative therapy, that of supplying an exogenous source of endothelial precursor cells (EPCs), may be optimal for cellular therapeutics to enhance vasculogenesis and collateralization around blocked/narrowed vessels to relieve ischemia. Clinical use of autologous patient-derived sources of stem cells is advantageous to avoid potential adverse allogeneic immune reactivity; however, the disadvantages include the need to subject the patient to stem cell collection at a time of active vascular disease.

Therefore, there is still a need to develop treatment modalities for both myocardial ischemia and peripheral vascular disease that can promote vasculogenesis in the ischemic tissue.

SUMMARY OF THE INVENTION

The invention provides cell-based methods for the treatment of ischemia in a subject in need thereof. In some aspects, the invention provides therapies for increasing blood flow to an ischemic tissue in a subject, such as, but not limited to, by promoting the formation of blood vessels. In one aspect, the invention provides therapies comprising the introduction into a patient of cells that can differentiate into endothelial cells or that promote the differentiation of cells from the subject into endothelial cells. Such cells comprise stem cells and progenitor cells. The cells may be isolated from bone marrow, peripheral blood, umbilical cord cells or from other sources.

One aspect of the invention provides a method for treating an ischemic tissue in a subject in need thereof, comprising administering to said subject a therapeutically effective amount of enriched human endothelial generating cells and enriched human mesenchymal stem cells.

A related aspect of the invention provides a method for increasing blood flow to an ischemic myocardium in a subject in need hereof, comprising administering to the subject a therapeutically effective amount of enriched human endothelial generating cells and enriched human mesenchymal stem cells.

Another aspect of the invention provides a method for inducing the formation of blood vessels in an ischemic myocardium in a subject in need thereof, comprising administering to the subject a therapeutically effective amount of enriched human endothelial generating cells and enriched human mesenchymal stem cells.

Yet another aspect of the invention provides a method for improving blood flow to an ischemic myocardium having an area of viable myocardium in a subject in need thereof, comprising administering to said subject a therapeutically effective amount of enriched $CD133^+/CD34^+$ endothelial precursor cells isolated from umbilical cord blood, wherein the $CD133^+/CD34^+$ endothelial precursor cells are administered by infusion into a coronary artery that is an epicardial vessel that provides collateral flow to said ischemic but viable myocardium in the distribution of a chronic totally occluded vessel, and wherein administering of the $CD133^+/CD34^+$ endothelial precursor cells results in improved blood flow to said ischemic myocardium. One embodiment of this method further comprises administering to said subject human mesenchymal stem cells. In another embodiment, the CD133+/CD34+ endothelial precursor cells are isolated from the bone marrow of the subject.

Another aspect of the invention provides a method for improving blood flow to an ischemic myocardium having an area of viable myocardium in a subject in need thereof, comprising (i) isolating bone marrow from the subject; (ii) selecting CD133+ cells from the bone marrow to generate an enriched population of CD133+ cells; (iii) holding the enriched population of CD133+ cells in a solution comprising buffered saline for 6-36 hours; (iv) administering the enriched population of CD133+ cells to the subject by intracoronary injection, thereby improving blood flow to said ischemic myocardium. In some embodiments, the solution further comprises serum from the subject, or soluble human fibronectin, hyaluronan or type I collagen, or a combination thereof. In another embodiment, the said method further comprises administering mesenchymal stem cells, such as those isolated from umbilical cord blood, to the subject by infusion into a coronary artery.

In certain aspects, the invention provides pharmaceutical formulations that may be administered to a subject, particularly a subject having an ischemic tissue. A formulation may comprise endothelial generating cells, mesenchymal stem cells, or both. Optionally, the endothelial generating cells are enriched from umbilical cord blood. Optionally, the mesenchymal stem cells enriched from bone marrow. In certain preferred embodiments, the formulation is designed for administration to a blood vessel by a catheter.

Another aspect of the invention provides kits comprising CD133+ cells, such as kits for the treatment of ischemia in a subject.

BRIEF DESCRIPTION OF THE DRAWINGS

FIG. 1 illustrates fluorescent cytochemical staining of endothelial precursor cells EPC derived from umbilical cord blood (UCB) under short-term endothelial-driving culture conditions. Panel A illustrates uptake of acetylated low-density lipoprotein (acLDL). Panel B illustrates adherence of *Ulex europaeus* agglutinin (UEA-1). Panel C illustrates composite dual staining for acLDL and UEA-1. Images were recorded using a confocal microscope at 40× magnification.

FIG. 15 illustrates ELISA analysis of active TGF-b1 in monocultured or co-cultured hMSCs and HUVECs. Monocultured hMSCs and HUVECs secrete latent TGF-b1 protein (A). Co-culture of hMSCs and HUVECs produces active TGF-b1 protein (B).

DETAILED DESCRIPTION OF THE INVENTION

I. Overview

Figure 2:
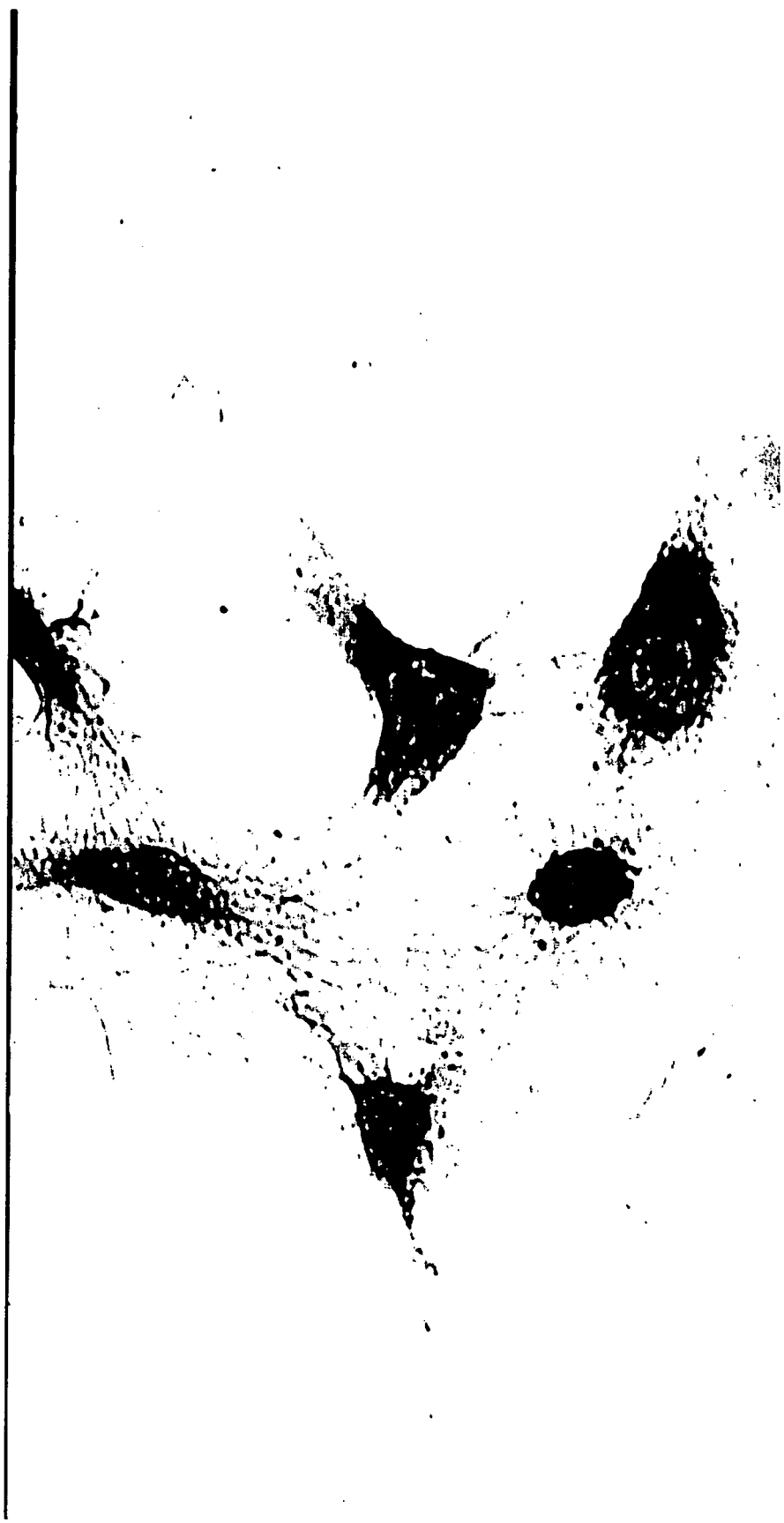
FIG. 2 illustrates staining of EPC derived from UCB for von Willebrand factor (vWF) and also illustrates the spindle-like morphology characteristic of EPCs. The cells were studied using phase contrast microscopy using a 40× magnification. Brown perinuclear stain is due to immunoperoxidase conjugated to secondary antibodies that reacted with perinuclear vWF particles.

The invention broadly relates to a cell-based therapy for the treatment of ischemic tissue. Ischemic tissue may be treated by increasing the blood flow to the tissue. Such increase in blood flow may be mediated, for example, by increasing the number of blood vessels which supply that tissue. The production of blood vessels is accomplished by two main processes: angiogenesis and vasculogenesis. Angiogenesis refers to the production of vascular tissue from fully differentiated endothelial cells derived from pre-existing native blood vessels. Angiogenesis is induced by complex signaling mechanisms of cytokines including vascular endothelial growth factor (VEGF), basic fibroblast growth factor (bFGF), and other mediators. This process is mediated by the encroachment of "activated" endothelial cells through the disrupted basement membrane into the interstitium possibly via an ischemic signal. "Therapeutic angiogenesis" refers to utilizing cytokines derived from gene or recombinant therapy, to induce or augment collateral blood vessel production in patients with ischemic vascular diseases.

In contrast, vasculogenesis, which until recently was believed to occur only in embryos, is the formation of vascular tissues in situ from endothelial precursor cells (EPCs) or angioblasts. Formation of blood islands or clusters of stem cells originating from a common ancestor, the hemangioblast, initiates the process. In these islands or clusters, peripherally located EPCs mature into the endothelium while the centrally located hematopoietic stem cells (HSCs) give rise to blood cells. As used herein, "therapeutic vasculogenesis" refers to neogenesis of vascular tissues by introduction of exogenous endothelial producing cells into the subject cells into a subject.

The invention generally provides methods of increasing blood flow to an ischemic tissue. More specifically, the invention provides methods for treating an ischemic tissue in a subject in need thereof, comprising administering to said subject a therapeutically effective amount of enriched human endothelial generating cells and enriched human mesenchymal stem cells. As used herein, human endothelial generating cells refers to cells capable of differentiating into human endothelial cells.

A related aspect of the invention provides a method for increasing blood flow to an ischemic myocardium in a subject in need hereof, comprising administering to the subject a therapeutically effective amount of enriched human endothelial generating cells and enriched human mesenchymal stem cells.

Another aspect of the invention provides a method for inducing the formation of blood vessels in an ischemic myocardium in a subject in need thereof, comprising administering to the subject a therapeutically effective amount of enriched human endothelial generating cells and enriched human mesenchymal stem cells.

Yet another aspect of the invention provides a method for improving blood flow to an ischemic myocardium having an area of viable myocardium in a subject in need thereof, comprising administering to said subject a therapeutically effective amount of enriched CD133$^+$/CD34$^+$ endothelial precursor cells isolated from umbilical cord blood, wherein the CD133$^+$/CD34$^+$ endothelial precursor cells are administered by infusion into a coronary artery that is an epicardial vessel that provides collateral flow to said ischemic but viable myocardium in the distribution of a chronic totally occluded vessel, and wherein administering of the CD133$^+$/CD34$^+$ endothelial precursor cells results in improved blood flow to said ischemic myocardium. One embodiment of this method further comprises administering to said subject human mesenchymal stem cells.

In one preferred embodiment of the methods described herein, the subject is a human. In another embodiment, the subject is an adult, a new born, an embryo or a fetus. In one embodiment of the methods described herein for treatment of a subject, the cells used in the therapies are isolated from the subjects own umbilical cord blood. Such umbilical cord blood maybe cryopreserved at the time the subject is born for use when needed. In one embodiment of the methods described herein, the treatment of the ischemic tissue, such as but not limited to ischemic myocardium, induces formation of blood vessels supplying blood to the ischemic tissue, blood flow to the ischemic tissue, oxygen supply to the ischemic tissue, or a combination thereof.

In one embodiment of the methods described herein, the human endothelial generating cells are human endothelial precursor cells. In one embodiment of the methods described herein, the endothelial generating cells are isolated from bone marrow, from peripheral blood, or more preferably, from umbilical cord blood. In one embodiment, the endothelial generating cells, such as endothelial precursor cells, are culture-expanded under endothelial cell-promoting culture conditions prior to administration to the subject. In another embodiment, the endothelial generating cells are enriched at least two-fold prior to the prior to administration to the subject. Enrichment can generally be achieved by removing at least some non-endothelial generating cells from a composition comprising both endothelial generating cells and non-endothelial generating cells, by propagating endothelial generating cells under culture conditions which increase their numbers relative to non-endothelial generating cells, or by a combination thereof. In one embodiment of the methods described herein, the endothelial generating cells are hemangioblasts, hematopoetic stem cells, or more preferably endothelial progenitor cells. In specific embodiments of the methods described herein, a combination of these cells are administered to the subject.

In an embodiment of the methods described herein, the endothelial generating cells, such as endothelial precursor cells, are $CD31^+$, $CD146^+$, $CD133^+$, $CD34^+$, $VE\text{-cadherin}^+$ or a combination thereof. In a specific embodiment, the endothelial generating cells are $CD133^+/CD34^+$ endothelial precursor cells. In other specific embodiments of the methods described herein, the endothelial generating cells, such as endothelial precursor cells, are autologous, allogenic, or HLA-compatible with the subject.

In specific embodiments of the methods described herein, the human mesenchymal stem cells are isolated from bone marrow or from umbilical cord blood, and may be culture-expanded prior their administration to the subject. In a specific embodiment, the mesenchymal stem cells are culture-expanded to enrich for cells containing surface antigens identified by monoclonal antibodies SH2, SH3 or SH4, prior to administering the human mesenchymal stem cells to the subject.

In specific embodiments of the methods described herein, the human mesenchymal stem cells are autologous, allogenic, or HLA compatible with the subject. The number of endothelial generating cells and/or mesenchymal stem cells administered to an individual afflicted with an ischemic tissue will vary according to the severity of the ischemia, the size of the tissue that is ischemic, and the method of delivery. In one embodiment of the methods described herein, the therapeutically effective amount of enriched human endothelial generating cells and enriched human mesenchymal stem cells is a safe and effective amount. In another specific embodiment, the amount of each cell type is at least $1\times10^4$ human endothelial generating cells. In another embodiment, the amount of enriched human endothelial generating cells and of enriched human mesenchymal stem cells administered to the subject in the methods described herein is between about $10^4$ and about $5\times10^8$ cells. The amount of cells administered to the subject will depend on the mode of administration and the site of administration. For example, a therapeutically effective cell dose via intracoronary injection (or intra-renal or intra-carotid) may be lower than that for intra-femoral injection. When both enriched human endothelial generating cells and enriched human mesenchymal stem cells administered to the subject, the ratio of the two cell types may be, for example, from about 20:1 to about 1:20, from about 10:1 to about 1:10, from about 5:1 to about 1:5, and form about 2:1 to about 1:2.

In embodiments of the methods described herein, administering to the subject comprises an infusion of cells into the subject. The infusion may comprise a systemic infusion of cells into the subject, or it may comprise an infusion of cells in the proximity of the ischemic tissue, so as to facilitate the migration of cells to the ischemic tissue. The infusion may also be performed on the blood vessels that supply blood to the ischemic tissue, or to blood vessels which remove blood from the ischemic tissue. In specific embodiments of the methods described herein, the infusion of cells into the subject comprises an infusion into bone marrow, an intra-arterial infusion, an intramuscular infusion, an intracardiac infusion, and intracoronary infusion, an intravenous infusion or an intradermal infusion. In one embodiment of the methods described herein, the human endothelial precursor cells and the human mesenchymal stem cells are administered to the subject by infusion into at least one coronary artery. In a specific embodiment of the methods described herein, the coronary artery is an epicardial vessel that provides collateral blood flow to the ischemic myocardium in the distribution of a chronic totally occluded vessel.

In one embodiment of the methods described herein, the subject afflicted with an ischemic tissue is in need of treatment for chronic myocardial ischemia. In other embodiments, the subject is in need of treatment for ischemia selected from the group consisting of limb ischemia, ischemic cardiomyopathy, myocardial ischemia, cerebrovascular ischemia, renal ischemia, pulmonary ischemia and intestinal ischemia. The methods described herein are not limited to ischemia in any particular tissue, but are applicable to any type of ischemia. For example, in one embodiment of the methods described herein, the subject suffers from ischemia in multiple tissues. In such embodiment, a systemic infusion of cells to the subject may be performed, or alternatively or in combination, one or more localized infusions near the ischemic tissue may be performed. In one embodiment of the methods described herein, the ischemic myocardium comprises an area of viable myocardium.

In some embodiments of the methods described herein, administration of the cells to the subject is performed using an intra-arterial catheter, such as but not limited to a balloon catheter, or by using a stent. Any method currently available for delivering cells to a subject may be used to administer cells to a subject in the methods described herein.

In some embodiments of the methods described herein, at least one recombinant polypeptide or at least one drug is further administered to the subject. In one embodiment, the recombinant polypeptide comprises a growth factor, a chemokine, a cytokine, or a receptor of a growth factor, a chemokine, or a cytokine. In preferred embodiments, the recombinant polypeptide promotes angiogenesis, vasculogenesis, or both. In some embodiments, the recombinant polypeptide promotes the proliferation, the differentiation or the ability of the endothelial generating cells or the mesenchymal stem cells to localize to the ischemic tissue or to interact with cells from the ischemic tissue. In specific embodiments, the recombinant polypeptide comprises VEGF, BFGF, SDF, CXCR-4 or CXCR-5.

In some embodiments of the methods described herein, the endothelial generating cells, such as endothelial progenitor cells, or the mesenchymal stem cells, or both, are genetically modified. In a specific embodiment, the cells are genetically modified to express a recombinant polypeptide. In one embodiment the recombinant polypeptide is a growth factor, chemokine or cytokine, or a receptor for growth factors, chemokines or cytokines. In another specific embodiment, the recombinant polypeptide is VEGF, bFGF, SDF, CXCR-4 or CXCR-5. In another embodiment, the recombinant polypeptide expressed by the genetically modified cells promotes the proliferation, the differentiation or the ability of the endothelial generating cells or the mesenchymal stem cells to localize to the ischemic tissue. In another embodiments, the genetic modification enhances the ability of the modified cells to interact with cells at the site of the ischemic tissue. In a related embodiment, the endothelial generating cells, such as endothelial progenitor cells, or the mesenchymal stem cells, or both, are non-genetically modified, such as with polypeptides, antibodies, or antibody binding proteins, prior to administration to the patient. In some embodiments, this treatment is intended to increase the localization of the modified cells to the ischemic tissue.

In some embodiments of the methods described herein, the endothelial generating cells are endothelial precursor cells. In one embodiment, the endothelial precursor cells are $CD133^+$ cells, $CD34^+$ cells, or more preferably $CD133^+/CD34^+$ cells.

In embodiments of the methods described herein, the endothelial generating cells, such as endothelial precursor cells, are expanded in culture prior to administration to the subject. In specific embodiments, the endothelial generating cells are culture-expanded under endothelial cell-promoting culture conditions prior to administration to the subject.

In preferred embodiments of the methods described herein, the endothelial generating cells, such as endothelial precursor cells, and the mesenchymal stem cells, are enriched prior to administration. By enrichment it is meant that the concentration of the cells relative to that of other cells is increased. Enrichment may be accomplished by removing other types of cells from the composition containing these cells, by culturing the cells under conditions which improve their proliferation over those of other cells, or by any method known in the art for enriching one cell type over another. In some embodiments, the cells used in the methods described herein are enriched at least about two-fold, about five-fold, about twenty-fold, about fifty-fold, about one hundred-fold, about five hundred-fold, about one thousand-fold, about five thousand-fold, about ten thousand-fold, or by about fifty thousand fold.

One aspect of the invention provides a composition for the treatment of ischemia in a subject, comprising a population of cells wherein at least 50% of the cells express CD133+, wherein the CD133+ cells are derived from umbilical cord blood, bone marrow, or peripheral blood, and wherein the CD133+ cells can differentiate into hematopoetic and endothelial cell lineages; and at least an additional component. In a preferred embodiment, the CD133+ cells are derived from cryopreserved and thawed umbilical cord blood. In some embodiments, the additional component is human serum, preferably human serum from the subject for which administrations of the cells is intended. In another embodiment, the additional component may comprise a component of human serum, such as human serum albumin. In another embodiment, the second component comprises a preservative, such as citrate phosphate dextrose adenine (CPDA) or heparin. In another embodiment, the second component is soluble human fibronectin. In a specific embodiment, the soluble human fibronectin is found a concentration of at least 1 ng/mL, or mote preferably more than 10 ng/ml. In another embodiment, the cell viability of the CD133+ cells is at least 10% greater in the presence of the fibronectin than in its absence.

In some embodiments of the compositions provided herein, the compositions are provided frozen or cryopreserved. In other embodiments, the composition comprises a desicated population of cells. One specific aspect of the invention provides a composition for the treatment of ischemia in a subject, comprising (i) a desiccated population of cells wherein at least 50% of the cells express CD133+, wherein the CD133+ cells are derived from cryopreserved and thawed human umbilical cord blood and wherein the CD133+ cells can differentiate into hematopoetic and endothelial cell lineages; and (ii) at least one carbohydrate, such as trehalose. The tetrahalose may be present at a concentration of at least 25 nM. Methods for generating desiccated cell populations is described, for example, in U.S. Pat. No. 6,528, 309.

In some embodiments of the methods described herein, the cells which are to be administered to the subject are incubated in a buffer, such as a saline buffer. In one preferred embodiment, the buffer comprises human blood serum isolated from the same subject who is the recipient of the therapy. Human serum may be isolated using standard procedures. A solution comprising human blood serum may also be used to thaw a sample of cells that has been cryopreserved. In some embodiments, the solution comprising human serum comprises between 1-20% human serum, or more preferably 5-15%.

Some aspect of the embodiments provides methods for inducing neovascularization in a subject in need thereof. There are numerous conditions that cause the necessity of a mammal to be in need of neovascularization. For example, the mammal may have a wound that requires healing. The wound may be an acute wound, such as those caused by burns and contact with hard and/or sharp objects. For example, patients recovering from surgery, such as cardiovascular surgery, cardiovascular angioplasty, carotid angioplasty, and coronary angioplasty all require neovascularization. The wound may also be a chronic wound. Some examples of chronic wounds include ulcers, such as vascular ulcers and diabetic ulcers. Inducing neovascularization from the cells described in the present invention is especially effective in increasing cardiac or peripheral (i.e. limb) vascularization. Therefore, the method is especially effective in treating cardiac and peripheral ischemia. Patients suffering from other conditions also require neovascularization. Such conditions include sickle cell anemia and thalassemia.

The cells of the present invention may be recruited into the site that requires neovascularization. For example, stem cells may be mobilized (i.e., recruited) into the circulating peripheral blood by means of cytokines, such as, for example, G-CSF, GM-CSF, VEGF, SCF (c-kit ligand) and bFGF, chemokines, such as SDF-1, or Interleukins, such as interleukins 1 and 8. Stem cells may also be recruited to the circulating peripheral blood of a mammal if the mammal sustains, or is caused to sustain, an injury.

Another aspect of the invention provides a method for improving blood flow to a peripheral arterial vascular bed having an area of ischemic but viable tissue in a subject in need thereof, comprising administering to said subject a therapeutically effective amount of enriched $CD133^+/CD34^+$ endothelial precursor cells isolated from umbilical cord blood, bone marrow or peripheral blood, wherein the enriched $CD133^+/CD34^+$ endothelial precursor cells are administered by catheter infusion into at least one artery that provides collateral flow to said tissue, and wherein administering of the $CD133^+/CD34^+$ endothelial precursor cells results in improved blood flow to said ischemic tissue. In a specific embodiment, the subject is afflicted with at least one ischemic condition selected from the group consisting of myocardial ischemia, myocardial infarction, angina pectoris, any cardiac surgical interventions, renal ischemia, circulatory insufficiency in extremities, ischemia-reperfusion injury, stroke, trauma and peripheral vascular disease (PVD). In a one preferred embodiment, the ischemic condition is renal ischemia and the artery is a renal artery.

Another aspect of the invention also provides a method for improving blood flow to an ischemic myocardium having an area of viable myocardium in a subject in need thereof, comprising administering to said subject a therapeutically effective amount of enriched $CD133^+/CD34^+$ endothelial precursor cells isolated from umbilical cord blood, bone marrow or peripheral blood, wherein the enriched $CD133^+/CD34^+$ endothelial precursor cells are administered by infusion into a coronary artery, wherein administering of the $CD133^+/CD34^+$ endothelial precursor cells results in improved blood flow to said ischemic myocardium. In a specific embodiment, the CD133+/CD34+ endothelial precursor cells are isolated from umbilical cord blood. In another specific embodiment, the coronary artery is an epicardial vessel that provides collateral flow to said ischemic but viable myocardium in the distribution of a chronic partially or totally occluded vessel.

Another aspect of the invention also provides method for improving blood flow to an ischemic peripheral arterial vascular bed having an area of viable skeletal muscle in a subject in need thereof, comprising administering to said subject a therapeutically effective amount of enriched CD133$^+$/CD34$^+$ endothelial precursor cells isolated from umbilical cord blood, bone marrow or peripheral blood, wherein the enriched CD133$^+$/CD34$^+$ endothelial precursor cells are administered by catheter infusion into a femoral artery that provides collateral flow to said skeletal muscle in the distribution of a chronic totally or partially occluded vessel, and wherein administering of the CD133$^+$/CD34$^+$ endothelial precursor cells results in improved blood flow to said skeletal muscle. In a specific embodiment, the CD133+/CD34+ endothelial precursor cells are isolated from umbilical cord blood.

An additional aspect of the invention provides a method for improving blood flow to an ischemic myocardium having an area of viable myocardium in a subject in need thereof, comprising administering to said subject a therapeutically effective amount of a composition comprising (i) enriched CD133$^+$ cells isolated from umbilical cord blood; and (ii) serum from the subject; wherein the enriched CD133$^+$ cells are administered by infusion into a coronary artery, and wherein administering of the CD133$^+$ cells results in improved blood flow to said ischemic myocardium. In a specific embodiment, the coronary artery is an epicardial vessel that provides collateral flow to said ischemic but viable myocardium in the distribution of a chronic partially or totally occluded vessel.

A method for improving blood flow to an ischemic myocardium having an area of viable myocardium in a subject in need thereof, comprising (i) isolating bone marrow from the subject; (ii) selecting CD133+ cells from the bone marrow to generate an enriched population of CD133+ cells; (iii) holding the enriched population of CD133+ cells in a solution comprising buffered saline for 6-36 hours; (iv) administering the enriched population of CD133+ cells to the subject by intracoronary injection, thereby improving blood flow to said ischemic myocardium. In a specific embodiment, the solution further comprises serum from the subject, such as serum derived from peripheral cord blood or from bone marrow blood. In another embodiment, the solution further comprises soluble human fibronectin, hyaluronan or type I collagen, or a combination thereof. In another specific embodiment, the intracoronary injection comprises injection into an epicardial vessel that provides collateral flow to said ischemic but viable myocardium in the distribution of a chronic partially or totally occluded vessel.

In another embodiment of the methods for improving blood flow to an ischemic myocardium having an area of viable myocardium in a subject in need thereof, step (iv) further comprises administering to the subject mesenchymal stem cells (MSCs) isolated from the subject's bone marrow, or more preferably, from umbilical cord blood. In some embodiments, the MSCs are administered by intracoronary injection. The MSCs be mixed with the CD133+ cells are mixed prior to administration into the subject, or they may be injected separately.

In another embodiment of the methods for improving blood flow to an ischemic myocardium having an area of viable myocardium in a subject in need thereof, at least one a cytokine, chemokine or growth factor is administered to the subject. Exemplary growth factors include bFGF or VEGF. In preferred embodiments, the cytokine, chemokine or growth factor promotes angiogenesis or cardiovascularization. Other embodiments further comprise administering to the subject an anticoagulant.

In another embodiment of the methods described herein for improving blood flow to an ischemic myocardium having an area of viable myocardium in a subject in need thereof, the CD133+ cells are CD133+CD34+KDR-CXCR4-cells. In some embodiments, at least 10%, 20%, 30%, 40%, 50%, 60%, 70%, 75%, 80%, 90%, 95%, 98%, 99% of cells in the enriched population are CD133+ cells. In a specific embodiments, the enriched population of CD133+ also contains the following percentages of cells having specific markers: CD133+ (60%-99%), CD34+ (75%-99%), KDR (EGFR2) (0-10%), CD105 (15%-30%) and CXCR4(2%-15%).

In one embodiment of the foregoing methods, the enriched population of CD133+ cells is not expanded in culture prior to administration into the subject. Alternatively, in one embodiment, after step (ii) and before step (iii), the enriched population of CD133+ cells is expanded in vitro under conditions that promote the formation of endothelial cells. In one embodiment, the conditions that promote the formation of endothelial cells comprise cell culture media comprising (a) FBS; (b) horse serum; (c) hydrocortisone; (d) stem cell growth factor (SCGF); (e) VEGF; or (f) a combination thereof. In one specific embodiment, the conditions that promote the formation of endothelial cells comprise cell culture media comprising (a) 5-15% FBS; (b) 5-15% horse serum; (c) 0.1-10 mM hydrocortisone; (d) 10-1000 ng/ml of stem cell growth factor (SCGF); (e) 5-500 ng/ml of VEGF; (f) or a combination thereof. In an exemplary embodiment, the conditions that promote the formation of endothelial cells comprise cell culture media comprising (a) 10% FBS; (b) 10% horse serum; (c) 1 mM hydrocortisone; (d) 100 ng/ml of stem cell growth factor (SCGF); (e) 50 ng/ml of VEGF; or (f) a combination thereof.

In one embodiment of the foregoing methods, the therapeutically effective amount of CD133+ cells comprises between $1 \times 10^4$ to $5 \times 10^8$ cells. In another embodiment, the therapeutically effective amount of the CD133+ cells is the minimum number of cells necessary for increased blood flow induction to the ischemic myocardium.

II. Definitions

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

III. Human Endothelial Generating Cells

The methods described herein comprise the use of endothelial generating cells (EGCs). ECGs comprise any cell which can differentiate into an endothelial cell. ECGs comprise embryonic stem cells, hemangioblasts, pluripotent stem cells, hematopoietic stem cells and endothelial precursor cells. In some embodiments of the methods described herein, the endothelial generating cells, such as endothelial precursor cells, are generated in culture from hematopoetic stem cells, hemangioblasts or embryonic stem cells.

In a preferred embodiment of the methods for therapeutic neovascularization of cardiovascular and/or peripheral ischemic tissues described herein, endothelial generating cells comprise endothelial precursor cells. In a preferred embodiment, the exogenous EPC cells are enriched for CD133$^+$ cells. The cell surface marker CD133$^+$ is also known as AC133. AC133 is a recently discovered marker for HSCs from peripheral blood, bone marrow, fetal liver and umbilical cord blood (Gehling et al., 2000, Blood. 95(10): 3106-12; Yin et al. 1997. Blood 90(12):5002-12; Buhring et al. 1999. Ann NY Acad SCI 99 872: 25-39; Majka et al. 2000. Folia Histochem Cytobiol. 38:53-63). Antibodies which recognize the CD133 antigen are described in U.S. Pat. NO. 5,843,633. In another embodiment, EPCs are CD34$^+$ cells. In yet another embodiment, the EPCs are CD133$^+$/CD34$^+$ cells. AC133$^+$ hematopoietic stem cells are of particular interest in studies directed to therapeutic angiogenesis, as these cells have been shown to differentiate into endothelial cells after short-term culturing.

Bone marrow, peripheral blood or umbilical cord blood (UCB) are potential sources of CD133$^+$ cells that can generate EPCs. Accordingly, the EPCs used in the methods described herein may be isolated from any of these three sources. A simple isolation technique, the collection of adherent cells after four days of culture of fresh UCB, produces a cell population with significant proliferative and colony forming potential as previously described (Mandel, D. et al. Blood 98 (11), 55b. (2001), the contents of which are hereby incorporated by reference in their entirety.

The data described in the Exemplification section supports morphological features of UCB-derived EPCs consistent with vascular endothelial cultures. After short-term culture in media designed to expand vascular endothelial cells, many of these cultured cells exhibit surface markers that are considered specific to endothelial cells including CD31 and CD146 (P1H12). Accordingly, in a preferred embodiment, the EPCs used in the methods described herein give rise to endothelial cells which express CD31 and CD146 (P1H12) after short-term culture in media designed to expand vascular endothelial cells. The majority of the cells derived from EPCs using the methods described herein endocytose acLDL and a minority exhibit lectin binding, two important cytochemical endothelial characteristics. In addition, culture expanded UCB EPC produce von Willebrand Factor (vWF).

The examples described herein demonstrate that infusions of EPCs culture-expanded from non-selected UCB or adult bone marrow are comparable as to their biologic effect to increase blood flow in a NOD.SCID study model of hind limb vascular injury. We have observed that both UCB and bone marrow-derived expanded EPC infusions significantly increase blood flow in the ischemic leg by day 14-post injury/ cell infusion above that of cytokine infusions alone. This biologic effect of UCB-derived EPCs is noteworthy given the fact that UCB EPC cell infusions do not contain stromal elements as observed in bone marrow-derived EPCs. Histological examination of tissue from the ischemic leg showed infiltration of cells displaying a mature endothelial surface marker CD31. Accordingly, Applicants have identified UCB as a stem cell source for EPCs comparable to that derived from adult bone marrow.

In comparing UCB versus adult bone marrow-derived EPCs Applicants have observed similarities but also significant differences in surface phenotype. Adherent cells stained for CD34 and mature endothelial-specific markers CD146 (MUC18 or MCAM), CD31 and VE-cadherin. Over 60% of the cultured adherent cells were positive for CD146 from both stem cell sources. Expression of CD31 was lower in bone marrow-derived EPC compared to UCB-derived cells. VE-cadherin was also expressed in a lower percentage of cells from bone marrow compared to UCB. Moreover, EPC derived from UCB showed higher expression of CD34 compared to bone marrow-derived EPC.

UCB-derived EPCs have distinct advantages as a stem cell source for EPC including greater potential lifespan and greater reparative proliferation, compared to existing models of therapeutic vasculogenesis using EPC derived from patient peripheral blood or bone marrow. The use of UCB as a stem cell source for EPCs is advantageous due to its high content of early CD133$^+$ stem cells that can differentiate into EPC under appropriate culture conditions, as well as its robust proliferative capacity, low immunogenicity, low infectious contamination (including virions), and "off the shelf" clinical application potential with diverse representation of histocompatibility genotypes in banked unrelated UCB.

In a preferred embodiment, CD133$^+$ EPCs are preferably isolated from umbilical cord blood. CD133$^+$ EPCs can be positively selected from isolated mononuclear cells from any of the foregoing sources by any method that produces an enriched population of CD133$^+$ EPCs. Several techniques are well known for the rapid isolation of CD133$^+$ cells such as, but not limited to, leucopheresis, density gradient fractionation, immunoselection, differential adhesion separation, and the like. As a non-limiting example, MNC can be obtained by density gradient centrifugation and labeled with magnetic bead-conjugated anti-CD133 antibody and passed through one or more magnetic columns to yield positively selected CD133$^+$ cells. Additionally or alternatively, MNC can be labeled with a fluorescent antibody to CD133 and sorted by a fluorescence activated cell sorter (FACS) to obtain CD133$^+$ cells. Yields and purity of the obtained CD133$^+$ cells can vary, depending on the source and the methods used to purifyng the cells. Purity obtained after one passage of labeled cells through a magnetic column can be, for example, 75%-85% and, after subsequent FACS, the purity can be increased to 95%-99%.

CD133+ cells may further be purified based on the expression of an additional cell surface molecule, such as CD34. For example, human CD133+ stem cells may be further purified by means of an anti-CD34 antibody, such as the anti-My-10 monoclonal antibody described by Civin in U.S. Pat. No. 5,130,144. The hybridoma cell line that expresses the anti-My monoclonal antibody is available from the American Type Culture Collection, 12301 Parklawn Drive, Rockville, Md. 20852, USA. Some additional sources of antibodies capable of selecting CD34+ cells include AMAC, Westbrook, Me.; Coulter, Hialea, Fla.; and Becton Dickinson, Mountain View, Calif. CD34+ cells may also be isolated by means of comparable antibodies, which may be produced by methods known in the art, such as those described by Civin in U.S. Pat. No. 5,130,144.

CD133+ cells may be further purified by negative selection i.e. removing cells which express a given cell marker. For example, cells expressing CD1, CD2, CD3, CD4, CD5, CD8, CD10, CD11b, CD13, CD14, CD15, CD16, CD19, CD20, CD24, CD25, CD28, CD29, CD33, CD36, CD38, CD41, CD41, CD56, CD66b, CD66e, CD69 or glycophorin A may be negatively selected.

The CD133$^+$ endothelial precursor cells can be allogeneic, autologous or HLA-compatible with the recipient. It is known that in vivo, heterologous, homologous and autologous EPC grafts incorporate into sites of active angiogenesis or blood vessel injury, i.e., they selectively migrate to such locations.

The selected CD133+ EPCs can be culture-expanded under endothelial cell-promoting culture conditions prior to the administering step. Alternatively, MNC from bone marrow, peripheral blood or umbilical cord blood can be cultured under short-term culture (e.g., about 24 hours) in endothelial cell-promoting culture conditions, and CD133+ cells selected during culture by selection techniques such as those described above. It is recognized that at least a portion of the CD133+ endothelial precursor cells can also have markers of mature endothelial cells such as, but not limited to, CD31+ and/or CD146+.

Several culture media suitable for promoting endothelial cell differentiation are known. As a non-limiting example, one such suitable medium, described in Kalka et al. (2000) PNAS 97: 3422-3427, is EC basal medium-2 (EBM-2) (Clonetics, San Diego) with 5% fetal bovine serum (FBS) and standard SingleQuot™ additives that include human VEGF-1, human basic fibroblast growth factor-2 (FGF), insulin-like growth factor-1 (IGF-1), hydrocortisone, ascorbic acid and heparin.

Additional methods and sources of isolating CD133+ cells are described, for example, in International PCT Application Nos. WO03/095631, WO99/37751, and WO01/94420, and U.S. patent Publication Nos. 2003/0091547, 2003/0199464 and 2002/0051762, the entire teachings of which are herein incorporated by reference.

On one embodiment of the methods described herein, the EGCs are genetically modified prior to administration to the subject. In one embodiment, EGCs are genetically modified to express a recombinant polypeptide, such as a growth factor, chemokine, or cytokine, or a receptor thereof. In another embodiment, the recombinant peptide is VEGF, BFGF, SDF, CXCR-4 or CXCR-5. In another embodiment, the genetic modification promotes angiogenesis, vasculogenesis, or both. EGCs may be modified, for example, using the methods commonly known in the art, such as by transfection, transformation or transduction, using recombinant expression vectors. The vector may be integrated into chromosomal DNA or be carried as a resident plasmid by the genetically modified ECG. In some embodiments, retroviruses are used to genetically modify the EGCs. Additional genes that may be introduced into the EGCs are described in International PCT Publication No. WO99/3775 1.

In some embodiments of the methods described herein, the endothelial generating cells comprise CD133+ cells. In specific embodiments of the compositions described herein which comprise CD133+ cells, at least 10% of the cells in the composition are CD133+ cells. In other specific embodiments, at least at least 15%, 20%, 25%, 30%, 35%, 40%, 45%, 50%, 55%, 60%, 65%, 70%, 75%, 80%, 85%, 90%, 95%, 96%, 97%, 98% or 99% of the cells in the composition are CD133+ cells.

IV. Human Mesenchymal Stem Cells/Stromal Cells

One aspect of the invention provides methods for treating an ischemic tissue in a subject in need thereof, comprising administering to said subject a therapeutically effective amount of enriched human endothelial generating cells and enriched human mesenchymal stem cells. Mesenchymal stem cells are the formative pluripotent blast cells found in the bone marrow and peripheral blood that are capable of differentiating into any of the specific types of connective tissues (i.e., the tissues of the adipose, areolar, osseous, cartilaginous, elastic, and fibrous connective tissues) depending upon various environmental influences. Mesenchymal stem cells are also commonly referred to as "marrow stromal cells" or just "stromal cells". Mesenchymal progenitor cells, are derived from mesenchymal stem cells and have a more limited differentiating potential, but are able to differentiate into at least two tissues (see for example, FIG. 1 of Minguell et al. 2001 Exp Biol Med (Maywood);226(6):507-20). As used herein, the term "mesenchymal stem cells" comprises mesenchymal stem cells, mesenchymal progenitor cells and marrow stromal cells.

Applicants have previously reported extensive research on methods to isolate, culture-expand and phenotypically characterize hMSCs, as well as their multi-lineage developmental potential and capacity to regulate a variety of other developmental events including angiogenesis (Fleming, J E Jr. et al. Dev. Dyn. 212, 119-132 (1998); Barry F P et al. Biochem. Biophys. Res. Commun. 265, 134-139 (1999)). Although hMSCs are rare, comprising about 0.01-0.0001% of the total nucleated cells of bone marrow, Applicants have perfected a cell culture methodology for their isolation from bone marrow, purification to homogeneity from other bone marrow cells and mitotic expansion in culture without loss of their stem cell potential (Haynesworth S E et al. Bone 13, 81-88 (1992)). Human adult MSC, although marrow-derived, do not express CD34 or CD45, but have been shown to express IL-6, -7, -8, -11, -12, -14, -15, M-CSF, flt-3 ligand (FL), and SCF in steady state, and do not express IL-3 and TGFβ. Exposure to dexamethasone results in decreased expression of LIF, IL-6 and IL-11 (Haynesworth S E et al. J. Cell Physiol. 166, 585-592 (1996)). Moreover, adhesion molecules expressed by stromal cells of importance in supporting early hemangioblasts, include fibulin-1 and fibulin-2, tenascin-C, stromal cell-derived factor 1 (SDF-1), and collagen type VI.

While not being bound by theory, it is believe that hMSCs home to sites of vascular injury and augment vasculogenesis in concert with early hemangioblasts, via secreted soluble factors and direct cell contact effects. Mesenchymal cells are known to constitutively secrete extracellular matrix-degrading enzymes, primarily matrix metalloproteinase 9, which promote endothelial cell invasion. In addition, mesenchymal cells secrete several pro angiogenic factors including VEGF, bFGF, IL-8, PDGF, and hematopoietic growth factors that promote endothelial cell migration, proliferation, and/or tube formation.

Mesenchymal stem cells for use in the methods according to the invention can be isolated from peripheral blood or bone marrow. A method for preparing hMSC has been described in U.S. Pat. No. 5,486,359. Furthermore, mesenchymal stem cells may also be isolated from umbilical cord blood, as described by Erices et al. 2000 Br. J Haematol 109(1):235-42. In a preferred embodiment of the methods described herein, when the mesenchymal stem cells are isolated from bone marrow or peripheral blood of the subject afflicted with ischemic tissue who will be the recipient of the treatment.

Several techniques are known for the rapid isolation of mesenchymal stem cells including, but are not limited to, leucopheresis, density gradient fractionation, immunoselection, differential adhesion separation, and the like. For example, immunoselection can include isolation of a population of hMSCs using monoclonal antibodies raised against surface antigens expressed by bone marrow-derived hMSCs, i.e., SH2, SH3 or SH4, as described, for example, in U.S. Pat. No. 6,387,367. The SH2 antibody binds to endoglin (CD105), while SH3 and SH4 bind CD73. Further, these monoclonal antibodies provide effective probes which can be utilized for identifying, quantifying and purifying hMSC, regardless of their source in the body. In one embodiment of the methods described herein, mesenchymal stem cells are culture expanded to enrich for cells expressing CD45, CD73, CD105, stro-1, or a combination thereof. In another embodiment, human mesenchymal stem cells are culture-expanded to enrich for cells containing surface antigens identified by monoclonal antibodies SH2, SH3 or SH4, prior to administering the human mesenchymal stem cells to the subject. A stro-1 antibody is described in Gronthos et al., 1996, J. Hematother. 5: 15-23. Further cell surface markers that may be used to enrich for human mesenchymal stem cells, such as those found in Table I, page 237 of Fibbe et al., 2003. Ann. N.Y. Acad. Sci. 996: 235-244.

The hMSC for use in the methods according to the invention can be maintained in culture media which can be chemically defined serum free media or can be a "complete medium", such as Dulbecco's Modified Eagles Medium supplemented with 10% serum (DMEM). Suitable chemically defined serum free media are described in U.S. Pat. No. 5,908,782 and WO96/39487, and complete media are described in U.S. Pat. No. 5,486,359. Chemically defined medium comprises a minimum essential medium such as Iscove's Modified Dulbecco's Medium (IMDM), supplemented with human serum albumin, human Ex Cyte lipoprotein, transferrin, insulin, vitamins, essential and non-essential amino acides, sodium pyruvate, glutamine and a mitogen. These media stimulate mesenchymal stem cell growth without differentiation. Culture for about 2 weeks results in 10 to 14 doublings of the population of adherent cells. After plating the cells, removal of non-adherent cells by changes of medium every 3 to 4 days results in a highly purified culture of adherent cells that have retained their stem cell characteristics, and can be identified and quantified by their expression of cell surface antigens identified by monoclonal antibodies SH2, SH3 and/or SH4.

On one embodiment of the methods described herein, the mesenchymal stem cells are genetically modified prior to administration to the subject. In one embodiment, the mesenchymal cells are genetically modified to express a recombinant polypeptide, such as a growth factor, chemokine, or cytokine, or a receptor which binds growth factors, chemokines, or cytokines. In another embodiment, the recombinant peptide is vascular endothelial growth factor (VEGF), hepatocyte growth factor (HGF), fibroblast growth factor (FGF), stromal cell-derived factor 1 (SDF-1), or interleukin 8 (IL-8). Mesenchymal stem cells may be modified, for example, using the methods disclosed in U.S. Pat. No. 5,591,625 or the methods described above for EGCs. In another embodiment, the genetic modification promotes angiogenesis, vasculogenesis, or both. In yet another embodiment, the mesenchymal cells are genetically modified to promote their differentiation into cardiomyocytes. The recombinant polypeptide may be, for example, VEGF or angiopoietin-1. U.S. patent Publication No. 2003/0148952 describes the use of angiopoietin-1 to recruit endothelial precursor cells. In another embodiment, the recombinant polypeptide is selected from the group consisting of leukemia inhibitory factor, IL-1 through IL-13, IL-15 through IL-17, IL-19 through IL-22, granulocyte macrophage colony stimulating factor (GM-CSF), granulocyte colony stimulating factor (G-CSF), macrophage colony stimulating factor (M-CSF), erythropoietin (Epo), thrombopoietin (Tpo), Flt3-ligand, B cell activating factor, artemin, bone morphogenic protein factors, epidermal growth factor (EGF), glial derived neurotrophic factor, lymphotactin, macrophage inflammatory proteins, myostatin, neurturin, nerve growth factors, platelet derived growth factors, placental growth factor, pleiotrophin, stem cell factor, stem cell growth factors, transforming growth factors, tumor necrosis factors, Vascular Endothelial Cell Growth Factors, and fibroblast growth factors, FGF-acidic and basic fibroblast growth factor.

In another embodiment of the methods described herein, the mesenchymal stem cells are modified prior to implantation into the patient so as to promote their targeting to the ischemic tissue. In a specific embodiment, the cells are coated with protein G and with an antibody which binds an antigen that is abundant in sites of ischemic injury.

V. Methods of Administration

In the methods described herein, the therapeutically effective amount of the endothelial generating cells, such as $CD133^+$ EPCs, and the therapeutically effective amount hMSCs, can range from the maximum number of cells that is safely received by the subject to the minimum number of cells necessary for either induction of new blood vessel formation in the ischemic tissue or for increasing blood flow to the ischemic tissue. Generally, the therapeutically effective amount of each endothelial generating cells and hMSCs is at least $1 \times 10^4$ per kg of body weight of the subject and, most generally, need not be more than $7 \times 10^5$ of each type of cell per kg. The ratio of $CD133^+$ EPCs to hMSCs can vary from about 5:1 to about 1:5. A ratio of about 1:1 is preferable. Although it is preferable that the hMSCs are autologous or HLA-compatible with the subject, the hMSCs can be isolated from other individuals or species or from genetically-engineered inbred donor strains, or from in vitro cell cultures.

The therapeutically effective amount of the $CD133^+$ EPCs and/or the MSCs can be suspended in a pharmaceutically acceptable carrier or excipient. Such a carrier includes but is not limited to basal culture medium plus 1% serum albumin, saline, buffered saline, dextrose, water, and combinations thereof. The formulation should suit the mode of administration. Accordingly, the invention provides a use of human endothelial producing cells, such as $CD133^+$ EPCs, for the manufacture of a medicament to treat an ischemic tissue in a subject in need thereof. In some embodiments, the medicament further comprises recombinant polypeptides, such as growth factors, chemokines or cytokines. In further embodiments, the medicaments comprise hMSCs. The cells used to manufacture the medicaments may be isolated, derived, or enriched using any of the variations provided for the methods described herein.

In a preferred embodiment, the endothelial generating cell, $CD133^+$ EPC and/or the HMSC preparation or composition is formulated in accordance with routine procedures as a pharmaceutical composition adapted for intravenous administration to human beings. Typically, compositions for intravenous, intra-arterial or intracardiac administration are solutions in sterile isotonic aqueous buffer. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

A variety of means for administering cells to subjects will, in view of this specification, be apparent to those of skill in the art. Such methods include injection of the cells into a target site in a subject. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the invention can be introduced into the subject at a desired location. In a preferred embodiment, cells are formulated for administration into a blood vessel via a catheter (where the term "catheter" is intended to include any of the various tube-like systems for delivery of substances to a blood vessel). The cells may be prepared for delivery in a variety of different forms. For example, the cells may be suspended in a solution or gel. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Modes of administration of the endothelial generating cells, such as the $CD133^+$ EPCs, and the hMSCs include but are not limited to systemic intracardiac, intracoronary, intravenous or intra-arterial injection and injection directly into the tissue at the intended site of activity. The preparation can be administered by any convenient route, for example by infusion or bolus injection and can be administered together with other biologically active agents. Administration is preferably systemic. Most preferably, the site of administration is close to or nearest the intended site of activity. In cases when a subject suffers from global ischemia, a systemic administration, such as intravenous administration, is preferred. Without intending to be bound by mechanism, endothelial generating cells such as $CD133^+$ EPCs and the hMSCs will, when administered, migrate or home to the ischemic tissue in response to chemotactic factors produced due to the injury.

In one embodiment, the endothelial generating cells such as the $CD133^+$ EPCs are co-administered simultaneously with the hMSCs. In another embodiment the hMSCs are administered before or after the injection of the endothelial generating cells. Administration of the EGCs or the mesenchymal stem cells/stromal cells may be carried out using the same mode or different modes of administration. For example, EPCs can be administered by intracoronary injection, while stromal cells might be administered intravenously.

Ischemic tissue that can be treated by the methods of the invention include, but are not limited to, limb ischemia, myocardial ischemia (especially chronic myocardial ischemia), ischemic cardiomyopathy, cerebrovascular ischemia, renal ischemia, pulmonary ischemia, intestinal ischemia, and the like.

In one embodiment of the methods described herein, a recombinant polypeptide or a drug is administered to the subject in combination with the administration of cells. The polypeptide or drug may be administered to the subject before, concurrently, or after the administration of the cells. In one preferred embodiment, the recombinant polypeptide or drug promotes angiogenesis, vasculogenesis, or both. In another embodiment, the recombinant polypeptide or drug promotes the proliferation or differentiation of the endothelial generating cells, of the mesenchymal stem cells, or of both. In one embodiment, the recombinant polypeptide is VEGF, BFGF, SDF, CXCR-4 or CXCR-5, or a fragment thereof which retains a therapeutic activity to the ischemic tissue.

In particular, the invention methods are useful for therapeutic vasculogenesis for the treatment of myocardial ischemia in humans. Administration of $CD133^+$ EPCs and hMSCs according to invention methods can be used as a sole treatment or as an adjunct to surgical and/or medical treatment modalities. For example, the methods described herein for treatment of myocardial ischemia can be used in conjunction with coronary artery bypass grafting or percutaneous coronary interventions. The methods described herein are particularly useful for subjects that have incomplete revascularization of the ischemic area after surgical treatments and, therefore, have areas of ischemic but viable myocardium. Subjects that can significantly benefit from the therapeutic vasculogenesis according to the methods of the invention are those who have large areas of viable myocardium jeopardized by the impaired perfusion supplied by vessels that are poor targets for revascularization techniques. Other subjects that can benefit from the therapeutic vasculogenesis methods are those having vessels of small caliber, severe diffuse atherosclerotic disease, and prior revascularization, in particular bypass grafting. Therefore, the therapeutic vasculogenesis according to the methods of the invention can particularly benefit subjects with chronic myocardial ischemia.

Although the stem cells can be injected directly into the area of ischemia, the stem cells are preferably infused into a coronary artery, preferably a coronary artery supplying the area of myocardial ischemia. Where the subject has a totally occluded vessel that would normally supply the area of the ischemic myocardium, the selected coronary artery for infusion is preferably an epicardial vessel that provides collateral flow to the ischemic myocardium in the distribution of the totally occluded vessel.

The therapeutically effective amount of the $CD133^+$ EPCs is a maximum number of cells that is safely received by the subject. Because the preferred injection route is intracoronary, and hMSCs in culture become larger than those originally isolated, the maximum dose should take into consideration the size of the vessels into which the cells are infused, so that the vessels do not become congested or plugged. The minimum number of cells necessary for induction of new blood vessel formation in the ischemic myocardium can be determined empirically, without undue experimentation, by dose escalation studies. For example, such a dose escalation could begin with approximately $10^4$/kg body weight of $CD133^+$ EPCs alone, or in combination with approximately $10^4$/kg hMSCs. Effective amounts of CD133+ cells sufficient to cause the desired neovascularization can be done based on animal data using routine computational methods. In one embodiment the effective amount is about $1.5\times10^5$ CD133+ cells per kg body mass to about $3\times10^5$ per kg body mass. In another embodiment the effective amount is about $3\times10^5$ per kg body mass to about $4.5\times10^5$ CD133+ cells per kg body mass. In another embodiment the effective amount is about $4.5\times10^5$ per kg body mass to about $5.5\times10^5$ CD133+ cells per kg body mass. In another embodiment the effective amount is about $5.5\times10^5$ per kg body mass to about $7\times10^5$ CD133+ cells per kg body mass. In another embodiment the effective amount is about $7\times10^5$ per kg body mass to about $1\times10^6$ CD133+ cells per kg body mass. In another embodiment the effective amount is about $1\times10^6$ per kg body mass to about $1.5\times10^6$ CD133+ cells per kg body mass. In one embodiment the effective amount of human CD133+ cells is between about $1.5\times10^6$ and $4.5\times10^6$ CD133+ cells per kg of the subject's body mass and In a preferred embodiment the effective amount is about 5×10⁵ CD133+ cells per kg of the subject's body mass.

In some embodiments of the methods described herein, the composition comprising the CD133+ cells is introduced into a vessel of the subject without substantially altering the arterial pressure. In other embodiments, the composition is introduced into a vessel by blocking arterial flow for an amount of time, such as from 5 seconds to two minutes, such that the injected cells can pool and adhere to the vessel. In one embodiment, a balloon catheter is used to allow pressure driven administration.

One aspect of the invention further provides a pharmaceutical formulation, comprising: (a) CD133⁺/CD34⁺ cells enriched from umbilical cord blood; (b) mesenchymal stem cells containing surface antigens identified by monoclonal antibodies SH2, SH3 or SH4 enriched from bone marrow; and (c) a pharmaceutically acceptable carrier. In some embodiments, the formulation comprises from 10⁴ to 10⁹ CD133⁺/CD34⁺ cells. In another embodiment, the composition comprises from 10⁴ to 10⁹ mesenchymal stem cells. In a further embodiment, the formulation is prepared for administration by a catheter.

VI. Kits Comprising CD133+ Cells

One aspect of the invention provides kits comprising populations of CD133+ cells. In one embodiment, the CD133+ cells are isolated from umbilical cord blood, from peripheral blood or from bone marrow. In some embodiments, at least 10%, 20%, 30%, 40%, 50%, 60%,70%,80%,90%,95%,98%, or 99% of the cells in the kit are CD133+ cells. In some embodiments, the kit further comprises at least one component of a closed sterile system. Components of the closed sterile system include, but are not limited to, needles, syringes, catheter based syringes, needle based injection devices, needle-less injection devices, filters, tubing, valves and cannulas. In a related embodiment, the kit comprise components for the removal of a preservative from the population of cells. Preservatives may include EDTA or cryopreservatives, such as DMSO. Such components include filters, syringes, vials, containers, tubing, etc.

In other embodiments, the kit further comprises packaging and instructions for administering the population of CD133+ cells to a subject in need thereof, such as to a subject suffering from an ischemic condition, such as from ischemic myocardium. In some embodiments, the kit further comprises at least an excipient wherein said excipient is suitable for intracoronary injection of the cell population. In a preferred embodiment, the excipient is a non nonpyrogenic excipient. Exemplary excipients include acacia [9000-01-5], 6-Methyl-1,2,3-oxathiazin-4(3H)-one-2,2-dioxide potassium salt [55589-62-3], Ethanolic acid [64-19-7], 1,2,3-Propanetricarboxylic acid, 2-acetyloxy, tributyl ester [77-90-7], 1, 2, 3-Propanetricarboxylic acid, 2-acetyloxy, triethyl ester [77-89-4], Serum albumin [9048-49-1], Ethanol [64-17-5], Alginic acid [9005-32-7] (CAS numbers are indicated in brackets).

In another embodiment, the kit further comprises an anticoagulant or a platelet aggregation inhibitor. In one embodiment, the platelet aggregation inhibitor comprises an inhibitor of GP IIb-IIIa, such as eptifibatide, sold as Integrillin®, or a thrombin inhibitor, such as Argatroban or Exanta® (ximelagatran). Other anticoagulants include heparin or agents, such as warfarin, which inhibiting vitamin K-dependent coagulation factors.

One specific aspect of the invention provides a kit comprising: (a) a population of cells isolated from umbilical cord blood in unit dosage form, wherein at least 10% of the cells in said population express CD133; and (b) an excipient wherein said excipient is suitable for intracoronary injection.

Another aspect of the invention provides a kit comprising: (a) a population of cells isolated from umbilical cord blood, wherein at least 10% of the cells in said population express CD133; and (b) closed sterile system suitable for intra-coronary injection. In a specific embodiment, the closed sterile system comprises needles, syringes, catheter based syringes, needle-based and needle-less injection devices.

The invention also provides a kit comprising: (a) a premeasured amount of cells isolated from umbilical cord blood, wherein at least 10% of the cells express CD133; and (b) at least one closed sterile system component suitable for intra-coronary injection.

The invention additionally provides (a) a premeasured amount of cells isolated from umbilical cord blood, wherein at least 10% of the cells express CD133; and (b) at least one anticoagulating agent. In one embodiment, the anticoagulating agent is an inhibitor of GP IIb-IIIa, thrombin or a vitamin K-dependent coagulation factor. In a specific embodiment, the anticoagulating agent is selected from the group consisting of eptifibatide, argatroban, ximelagatran, warfarin and heparin.

The invention also provides a kit comprising: (a) at least two vials each containing a premeasured amount of cells isolated from umbilical cord blood, wherein at least 10% of the cells express CD133; and (b) at least one closed sterile system component suitable for intra-coronary injection; wherein the first vial is used for pretesting and/or quality control purposes and wherein the cells in the second vial are injected into a subject in need thereof. Pretesting and/or quality control purposes include, but are not limited to, testing the viability of the cells in the sample, assaying the concentration of the cells in the sample, testing the sterility of the sample or testing the immunocompatibility of the population of cells with a subject. Additional testing may comprise determining the presence of certain antigens in the cell population, such as HLA alleles, by immuno-based assays or by determining the DNA sequence of a gene in the sample.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999.

EXEMPLIFICATION

The invention now being generally described, it will be more readily understood by reference to the following examples, which are included merely for purposes of illustration of certain aspects and embodiments of the present invention, and are not intended to limit the invention, as one skilled in the art would recognize from the teachings herein-above and the following examples, that other stem cell sources and selection methods, other culture media and culture methods, other dosage and treatment schedules, and other animals and/or humans, all without limitation, can be employed, without departing from the scope of the invention as claimed.

Example 1

Isolation and Characterization of Endothelial Precursor Cells from Umbilical Cord Blood and Adult Bone Marrow.

Mononuclear cells were isolated from umbilical cord blood (UCB) or adult bone marrow (BM) and placed in short-term culture under conditions supportive of the development of endothelial precursor cells (EPC). Adherent cells recovered from the cultures were found to exhibit EPC characteristics, as analyzed using multiple in vitro assays, including cytochemistry, flow cytometry, microscopic morphology and immunostaining.

1) Isolation of Cells

Mononuclear cells (MNC) from fresh UCB or BM were isolated using density gradient centrifugation. EPC cells were isolated expanded in cell culture according to the method of Kalka et al. (2000) PNAS 97: 3422-3427. Briefly, the MNC were plated on human fibronectin coated tissue culture flasks at a density of $4$-$6 \times 10^6$ cells/ml (UCB MNC) or $1$-$2 \times 10^6$ cells/ml (BM MNC) in EC basal medium-2 (EBM-2) (Clonetics, San Diego) with 5% fetal bovine serum (FBS) and standard SingleQuot™ additives that included human VEGF-1, human fibroblast growth factor-2 (FGF), insulin-like growth factor-1 (IGF-1), hydrocortisone, ascorbic acid and heparin. Non-adherent cells were removed by washing with phosphate-buffered saline (PBS) after 4 days of culture and the medium was changed every fourth day thereafter. During the second week of culture, the adherent cells adopted the spindle-like morphology characteristic of EPCs.

At day 6-7, cells were trypsinized and counted. The yield of adherent cells from UCB cultures was, on average, 2.5%±0.4% of the initial MNC input, compared to a yield of 21.5%±3.7% obtained from BM MNC.

2) Cellular Staining of Adherent Cells for EPC Characteristics a) Two principal cytochemical staining features of mature endothelial cells are the adherence of specific lectin proteins, such as *Ulex europaeus* agglutinin (UEA)-1, and the uptake of acetylated low-density lipoprotein (acLDL). Fluorescent microscopy of adherent cells was performed to detect dual binding of FITC-labeled UEA-1 (Sigma) and 1,1'-dioctade-cyl-3,3,3',3'-tetramethylindocarbocyanine (DiI)-labeled acLDL (Biomedical Technologies, Stoughton, Mass.).

Adherent cells were first incubated with acLDL at 37° C. and fixed with 1% paraformaldehyde for 10 min. After washes, the cells were reacted with UEA-1 (10 µg/ml) for one hour. After the staining, samples were viewed at 40× with a confocal microscope set to record total cell fluorescence.

FIG. 1 illustrates fluorescent microscopy images showing cytochemical staining of UCB-derived EPC. It was found that the majority of the cells exhibited uptake of acLDL (A). A smaller proportion exhibited positive staining for UEA-1 lectin (B). Composite dual staining results for both cytochemical stains simultaneously are displayed in (C). Cells demonstrating double-positive fluorescence were identified as differentiating EPCs.

A comparison of the uptake of acLDL and morphology of EPC cells derived from both BM and UCB was determined. During the second week of culture, cells derived from both sources displayed uptake of acLDL and exhibited similar morphologic features (data not shown).

b) von Willebrand factor (vWF) is a well-characterized multimeric glycoprotein synthesized by vascular endothelial cells and megakaryocytes. Adherent cells cultured from UCB were stained for vWF. Slides with surface adherent cells were fixed in room temperature acetone for 10 min. and air dried. The cells were then reacted with a polyclonal rabbit anti-human Factor VII related antigen commercially available from Dako (Carpinteria, Calif.). Detection of cells binding the antibody was achieved using routine horse-radish peroxidase labeled streptavidin-biotin technology (LSAB2, Dako) and 3,3-diaminobenzidine as the chromogen. Staining was viewed by phase contrast microscopy using a magnification of 40×.

As illustrated in FIG. 2 the non-selected adherent cells cultured from UCB exhibited a distinct endothelial staining pattern. The brown perinuclear stain is due to immunoperoxidase conjugated to secondary antibodies that are reacting with perinuclear vWF particles. Human umbilical vein endothelial cells (HUVECS) were stained as positive controls, and fibroblasts as negative controls (data not shown).

Figure 3:
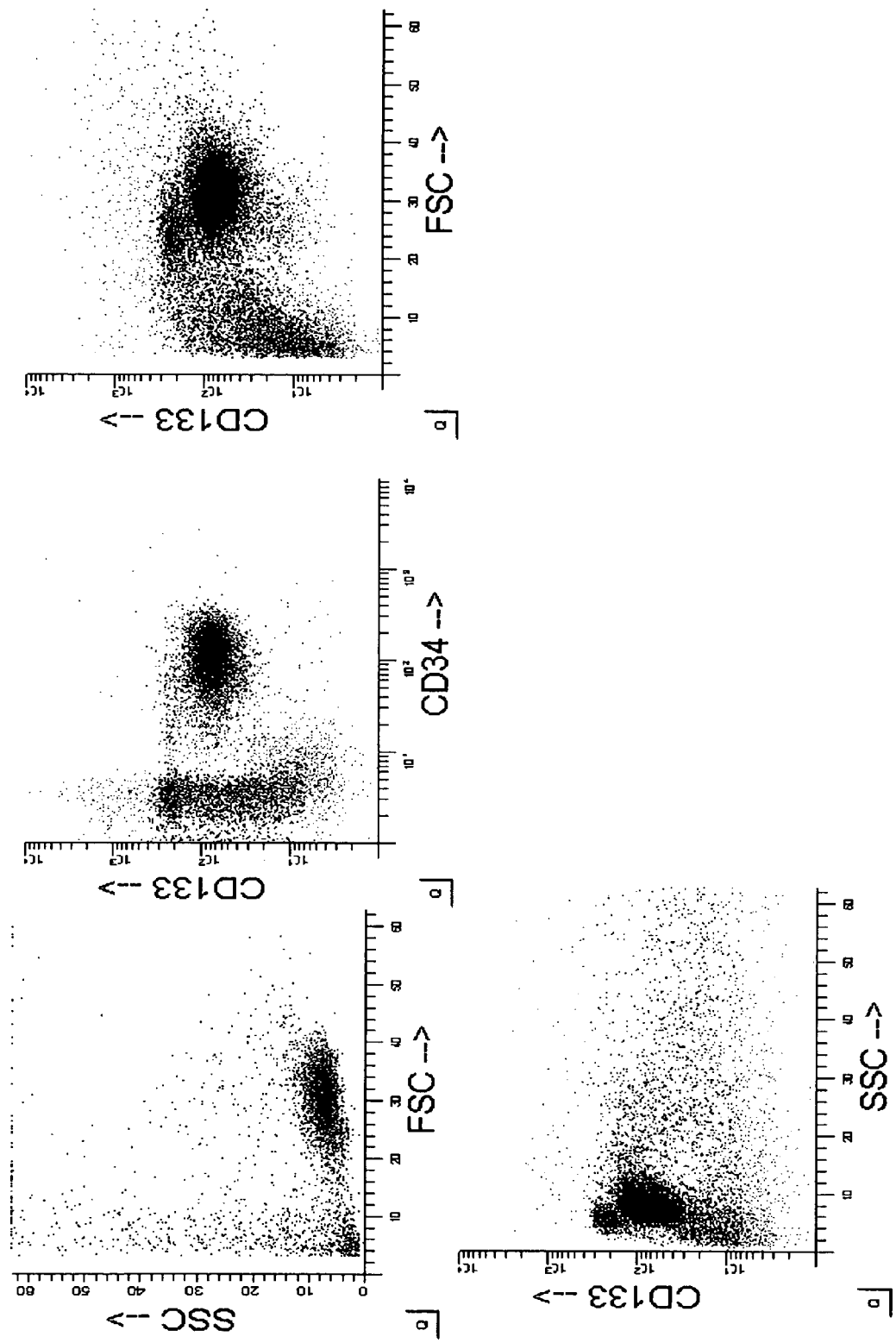
FIG. 3 illustrates flow cytometry analysis of the surface phenotype of CD133+ cells selected from UCB. FSC gain was increased for better resolution of very small cells. Distinct populations of CD133+/CD34− cells (100) and CD133+/CD34+ cells (200) were identified. No gating was applied.
Figure 4:
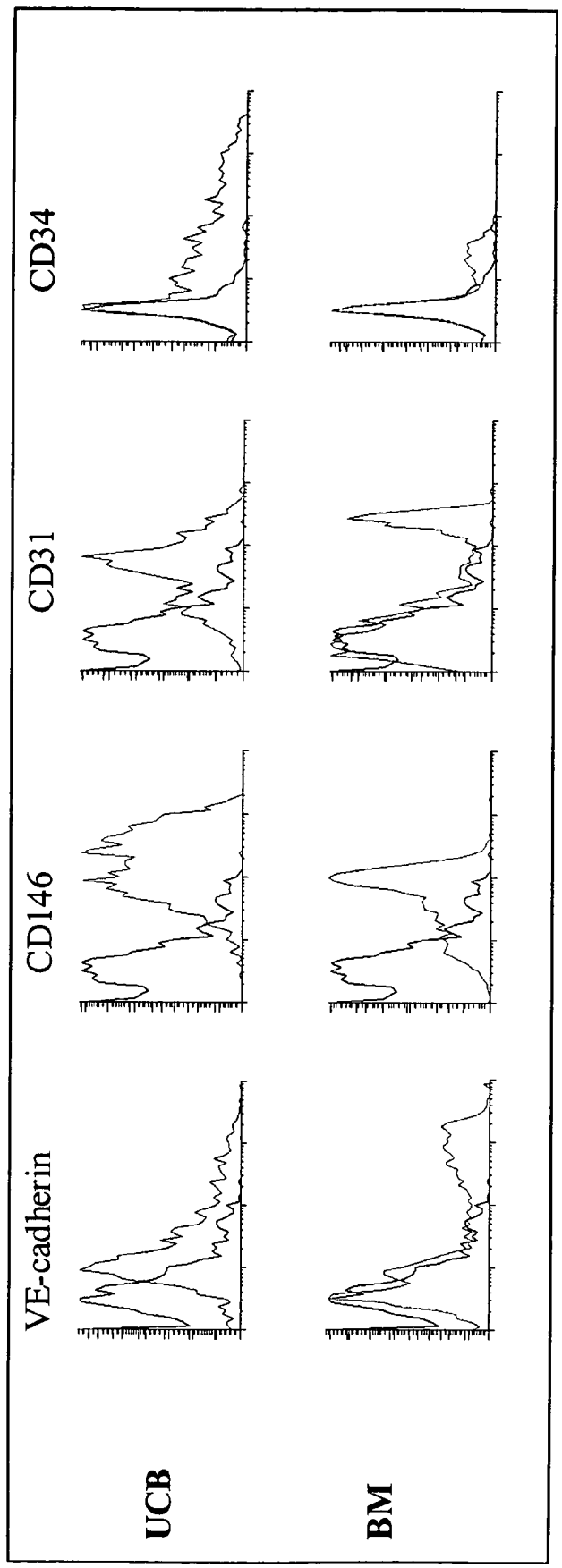
FIG. 4 illustrates flow cytometry analysis of a comparison of endothelial cell characteristics of EPC cells derived from UCB and human bone marrow (BM) after 19 days and 12 days of culture in endothelial-driving culture conditions. Adherent cells were trypsinized and stained for CD34 and endothelial-specific markers VE-cadherin, CD146 and CD31. The non-stained control is shown in black. The stained cells are shown in gray.

3) Flow Cytometry Analysis of EPC Cells Derived from UCB a) Selection and Phenotyping of CD133$^+$ cells:

$50 \times 10^6$ MNC from UCB were labeled with magnetic bead-conjugated anti-CD133 antibody (Miltenyl) and passed through two consecutive magnetic columns to yield $0.1 \times 10^6$ of positively selected CD133$^+$ cells. The selected CD133$^+$ cells were characterized by flow cytometry and staining for CD34 and CD133. FIG. 3 illustrates distinctly identified populations of CD133$^+$/CD34$^-$ cells (100) and CD133$^+$/CD34$^+$ cells (200), as displayed versus size (Forward Scatter, FSC) and granularity (refractivity Side Scatter, SSC). FSC gain was increased for better resolution of very small cells. No gating was applied.

b) Phenotyping of Unselected EPC Cells Derived from UCB and BM:

UCB cells were cultured for 19 days and BM cells were cultured for 12 days in EMB-2 media. Adherent cells were trypsinized and stained for CD34 and mature endothelial-specific markers CD146 (P1H12, MUC18 or MCAM), CD31 and human vascular endothelium (VE)-cadherin. As illustrated in FIG. 4, over 60% of the cultured adherent cells were positive for CD146. Expression of CD31 was 25% in BM derived EPC, compared to 50% in UCB derived cells. However, CD31 staining was brighter in BM. VE-cadherin was expressed in 10% of cells from BM compared to 24% in the cells from UCB. EPC derived from UCB showed expression of CD34 in 25% of cells, compared to 10% of the BM derived EPC.

In summary, the foregoing studies demonstrated that non-selected UCB and BM cells rapidly proliferate and expand under endothelial cell culture conditions. These UCB and BM derived EPC exhibit multiple endothelial characteristics.

Example 2

Transplantation of UCB and BM-Derived EPC in an in vivo Model

In vivo studies of neovascularization in a murine hind limb ischemia model, in NOD/SCID mice, were performed. The results illustrate that UCB is an optimal source of EPC. Although UCB lacks stromal elements present in BM, EPC from UCB demonstrated an equivalent biological effect in the in vivo model to that exerted by EPC derived from BM sources.

1) Treatment Groups. All procedures were performed in accordance with Case Western Reserve University's Institutional Animal Care and Use Committee. NOD/SCID mice, age 10-15 weeks were used in this example. Prior to surgery, the mice were irradiated with 2.5 Gy from a Cesium-137 source to further reduce rejection of injected human cells. The mice were fasted over night but allowed free access to water. They were then anesthetized with intraperitoneal injection of a combination of ketamine and pentobarbital. Under sterile conditions, a small skin incision was made in right groin area. The right femoral artery was exposed, ligated along with adjacent branches (with #000 silk) and transected. Special care was given not to ligate the femoral vein and femoral nerve. The skin incision was then closed with continuous suture fashion (#000 silk). After femoral artery ligation, the mice were divided into four groups. Group 1 animals received an intracardiac injection of $1 \times 10^6$ (in 0.02 ml of media) adherent (EPC) UCB cells harvested at day 7 of culture. Group 2 animals received intracardiac injection of $1 \times 10^6$ of adherent (EPC) BM cells harvested at day 7 of culture. Group 3 and Group 4 animals similarly received 0.02 ml. of complete EBM-2 medium or saline alone, respectively. Immediately after surgery and injection of cells, baseline blood blow of both the ischemic right leg and the non-operated left leg was measured using a laser Doppler flowmeter (Laser flowmeter ALF21D, Advance Company LTD, Tokyo, Japan). Laser Doppler measurements were repeated at 7 days, 14 days and 28 days after the surgery. A ratio of perfusion in the ischemic/healthy limb was used to compare neovascularization in the three study groups.

2) Comparison of Perfusion Ratios in Animals Treated with EPC from UCB or BM

Figure 5:
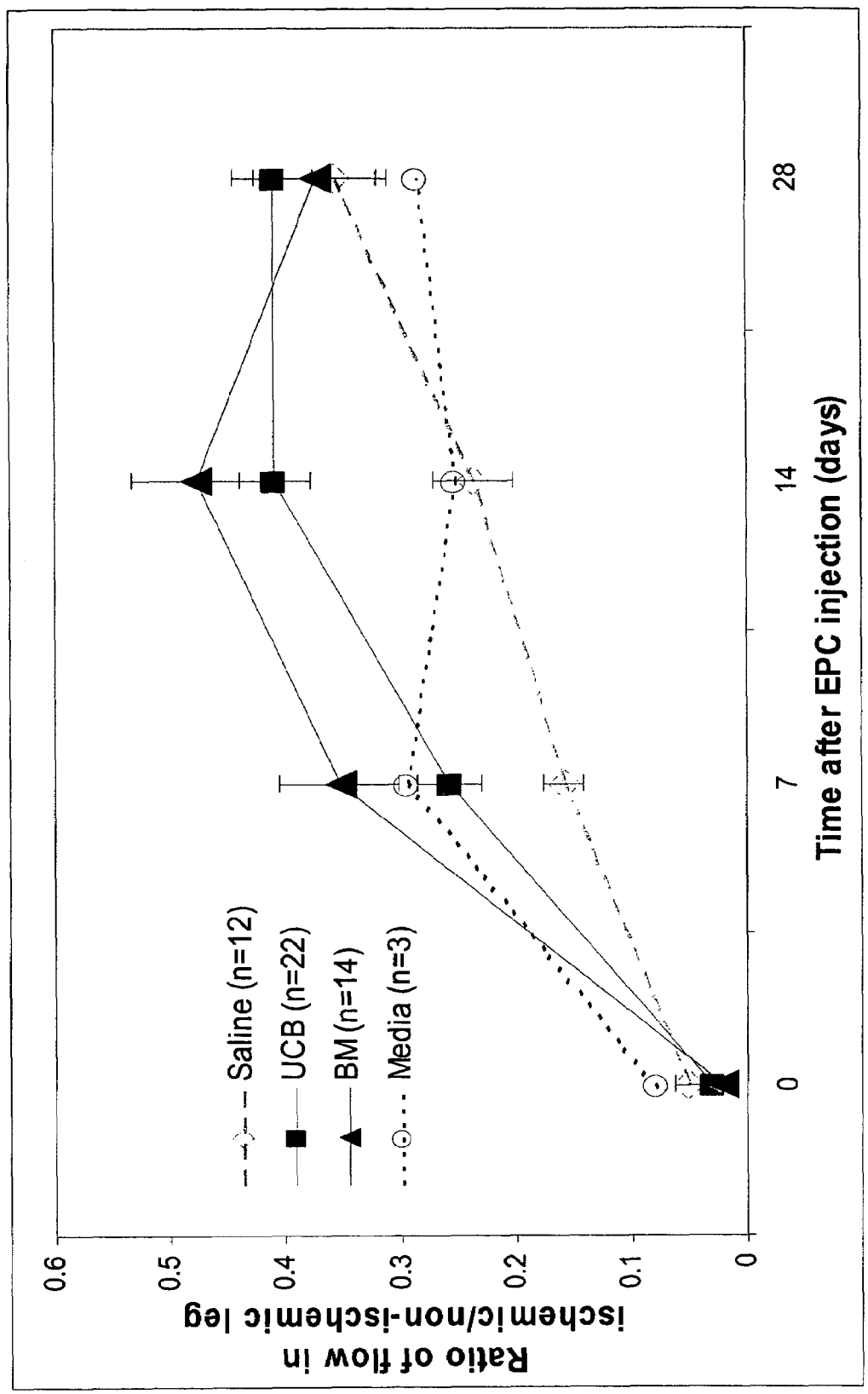
FIG. 5 depicts the results of neovascularization achieved by transplantation of UCB—and BM-derived EPC into an in vivo mouse hind limb ischemia model. NOD/SCID mice underwent femoral artery ligation and excision followed by injection of saline, medium or cells cultured for 7 days in endothelial-driving culture conditions. Laser Doppler measurements were taken post-op and then every week under the same conditions. Depicted is a comparison of the perfusion ratio between the ischemic and non-ischemic let.

FIG. 5 illustrates a comparison of the perfusion ratio between the ischemic and non-ischemic leg. Immediately following femoral ligation the perfusion ratios were 0.057±0.011 (control group injected with EBM-2 medium only), 0.029±0.007 (UCB-derived EPC) and 0.020±0.004 (BM-derived EPC) showing reduced perfusion in all groups. After 14 days, there was a statistically significant higher blood flow in the injured leg in study groups receiving UCB-derived EPC compared to the control group and between the BM-derived EPC group and the control group (p<0.001). Perfusion ratios in the control group remained low, with a ratio of 0.24±0.032 (n=14), compared to a ratio of 0.41±0.031 (n=22) in the group receiving UCB-derived EPC (p=0.0008) and a ratio of 0.48±0.039 (n=14) in the group receiving BM-derived EPC. At day 14 there was no significant difference in the ratios between the two sources of EPCs (p=0.18). Subsequent measurements at time point 28 days were notable for improvement in Doppler blood flow in control animals rendering perfusion ratios equalized when comparing the control group and mice receiving cell infusions.

3) Histological Assessment of Ischemic Hindlimb in Treatment Groups

Figure 6B:
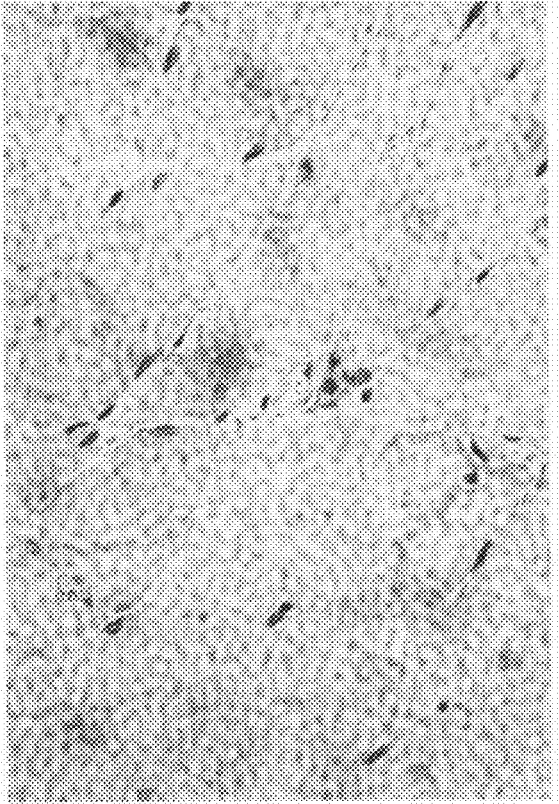
FIG. 6 illustrates a histological assessment of the ischemic hind limb at 28 days after surgery. The hind limb of the ischemic leg of the mouse injected with UCB-derived EPC showed positive CD31 staining, indicated by the white arrows. The control mouse, injected with medium only, was negative for CD31.
Figure 6A:

Tissue from the lower calf muscle of both hind limbs was harvested at day 28 for histological evaluation. The samples were fresh frozen in liquid nitrogen and fixed in formalin. Frozen sections of 6 μm thickness were mounted on saline-coated glass slides and stained using immunohistochemistry techniques to identify incorporation of EPCs derived from human cells by staining with anti-human CD31 antibody. As illustrated in FIG. 6, specimens from mice that were injected with UCB EPCs showed positive staining for CD31, where the control mice injected with complete EMB2 medium did not. Healthy limbs of all groups did not show positive CD31 staining (data not shown). The specimens from the BM EPC-injected mice showed similar results (data not shown).

Example 3

Selection and Purification of CD133$^+$ Cells from UCB

Figure 7:
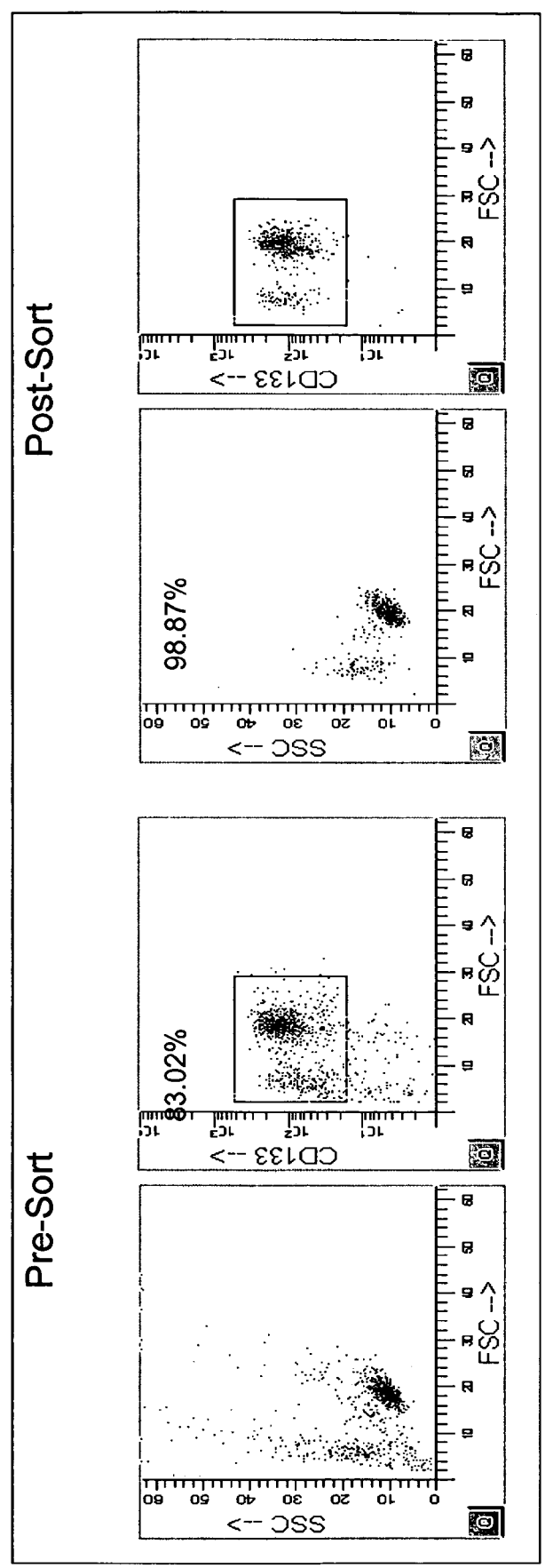
FIG. 7 illustrates the results of isolation and purification of CD133+ cells from UCB. Mononuclear cells (MNC) were labeled with anti-CD133 conjugated magnetic beads, followed by automated sorting through magnetic columns (Automacs, Miltenyi). The yield of the labeled CD133+ cells after passage through one magnetic column was routinely about 0.4% of the MNC cells, with a purity ranging between 75% and 85% (83.02% illustrated). After staining with CD133-PE, the cells were FACS sorted for PE fluorescence, raising the purity to 98.87%, with a final yield of 0.1% of the initial MNC input. No gating was applied.

For isolation and purification of CD133$^+$ cells, mononuclear cells were isolated from UCB as described above and were labeled with CD133$^+$ conjugated magnetic beads, followed by automated sorting through magnetic columns (Automacs, Miltenyi). By passaging the labeled cells through a single column, the routine yield was 0.4% of the original MNC, with a purity of CD133$^+$ cellsranging between 75% and 85%. By passage of the MNC through two consecutive magnetic columns, the purity could be raised to 91.2% CD133$^+$ cells, but the yields dropped to 0.2%. Further purification attempts were made by fluorescence-activated cell sorting (FACS). CD133$^+$ cells were isolated by passage through one magnetic column, stained with CD133-phycoerythrin (PE)-conjugated antibody and further purified by FACS. As illustrated in FIG. 7, the resulting purity after passage through one magnetic column was 83.02% CD133$^+$ cells. After FACS, the purity was increased to 98.87%, with a final yield of 0.1% of the initial MNC input.

Example 4

Culture-Expansion and Characterization of Purified CD133$^+$ Cells

1) Flow Cytometry Analysis of Surface Markers of CD133$^+$ Cells in Endothelial Cell-Driving Cytokines or Hematopoietic Cell-Driving Cytokines Purified CD133$^+$ cells isolated according to Example 3 were cultured either in hematopoiesis-driving cytokines or in cytokines that have been reported to generate endothelial cells from CD133$^+$ cells. (Gehling, U. M. et al. Blood 95(10): 3106-3112.) Briefly, for hematopoiesis-driving conditions, the CD133$^+$ cells were plated on a 96-well plate at a concentration of $0.2 \times 10^6$ cells/well/condition and incubated for 24 hours in either medium alone (Iscove's Modified Dulbecco's Medium, IMDM) with 2% FBS, or in hematopoietic culture medium (IMDM), 30% FBS, 50 ng/ml of stem cell factor (SCF), 20 ng/ml of human granulocyte-macrophage colony stimulating factor (GM-CSF), granulocyte colony stimulating factor (G-CSF), interleukin-3 (IL-3), IL-6, and 3 U/ml of erythropoietin). For endothelial cell-driving conditions, $0.2 \times 10^6$ CD133$^+$ cells were similarly plated and incubated in endothelial culture medium (IMDM, 10% FBS, 10% horse serum 1 mM hydrocortisone, 100 ng/ml of stem cell growth factor (SCGF), and 50 ng/ml of VEGF). After 24 hours of incubation, the cells were analyzed by flow cytometry for the hematopoietic surface markers CD34 and CD45, as well as for expression of BCL-2 and p21, which are cell cycle and apoptosis-regulating proteins, respectively, shown to play a role in regulation of the fate of HSC. For example, $p21^{cip1/waf1}$ is an inhibitor of cyclin-dependent kinases and mediates cell cycle arrest in G1. It has been shown that in $p21^{cip1/waf1}$ deficient mice there is increased proliferation of HSC under normal homeostatic conditions and exhaustion of the stem cell pool, suggesting that $p_{21}{}^{cip1/waf1}$ may be a molecular switch governing the entry of HSC into the cell cycle. Over expression of the anti-apoptotic protein BCL-2 in the hematopoietic compartment of transgenic mice has been shown to improve numbers of HSC as well as in vitro plating capacity, and maintained HSC in a more quiescent cell cycle status.

Figure 8:
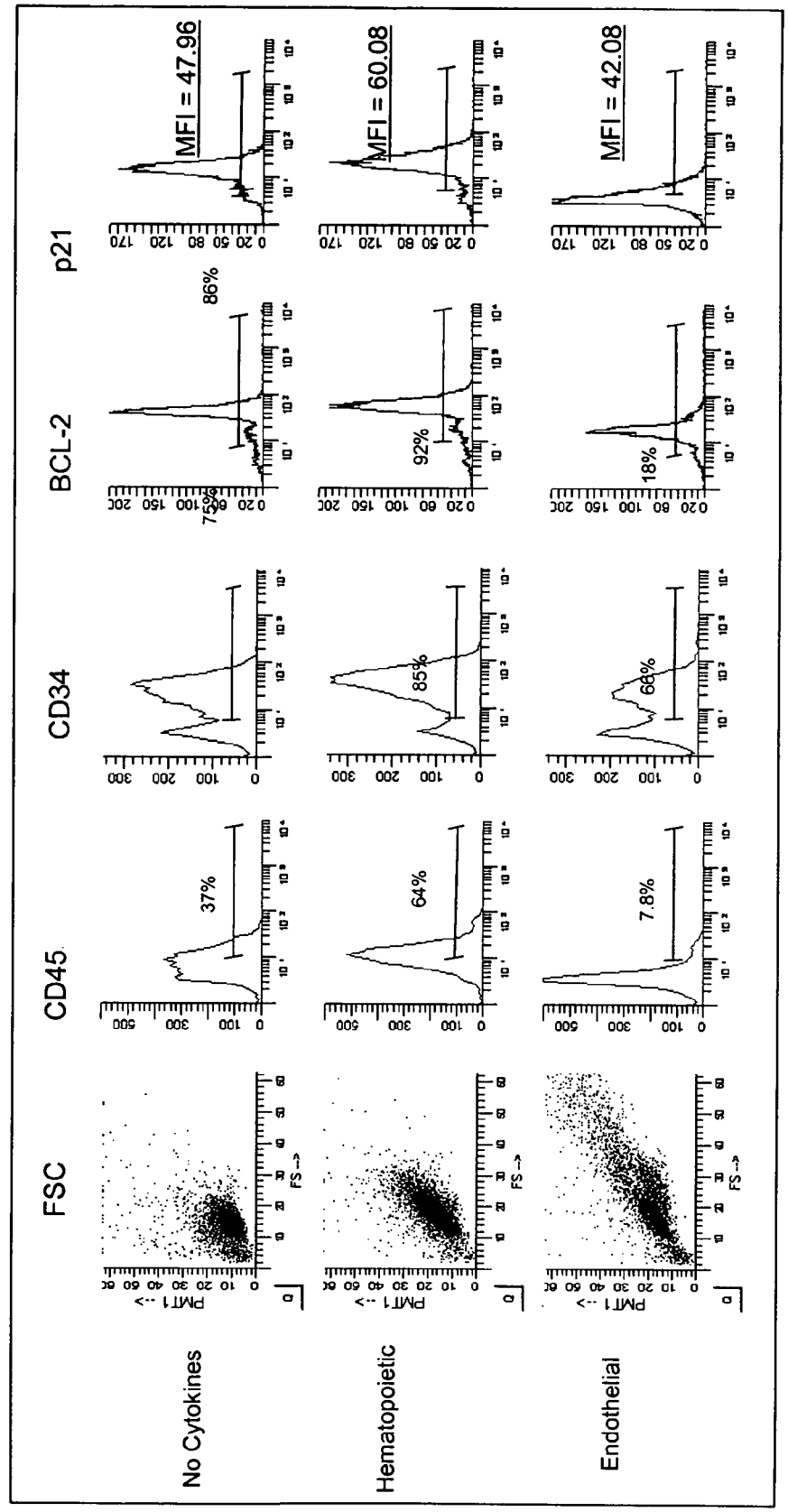
FIG. 8 illustrates differential expression of CD45, CD34, BCL-2 and p21 in purified CD133+ cells after 24 hours of culture under hematopoietic-driving or endothelial-driving conditions. The percentages are of the total cells analyzed.

The results of flow cytometry, illustrated in FIG. 8, show the intensity of expression in the total cells expressed as mean fluorescence intensity (MFI) or percentage of total cells analyzed. CD45 and CD34 expression were strongly increased after 24 hours of culture in hematopoiesis-lineage specific cytokines. CD45 expression was lost in endothelial cytokines, suggesting that the cells have already started differentiation away from the hematopoietic lineage. Expression of both p21 and BCL-2 proteins was increased in hematopoietic cytokine conditions. However, expression of both proteins decreased significantly in endothelial cytokine conditions, again suggesting that the two cell populations have already started differential gene expression programs.

2) Cell Cycle Analysis in Freshly Isolated or 24 Hour Cultured CD133+ Cells from UCB.

Cell cycle stages were analyzed in CD133+ cells freshly isolated as in Example 3, as well as in CD133+ cells after 24 hours of culture in medium alone, or under hematopoietic- or endothelial-driving conditions, as described above, or under hematopoietic conditions for 72 hours. Cells were fixed, permeabilized, and DNA stained with Hoechst under standard conditions, and analyzed for cell cycle stages.

Figure 9:
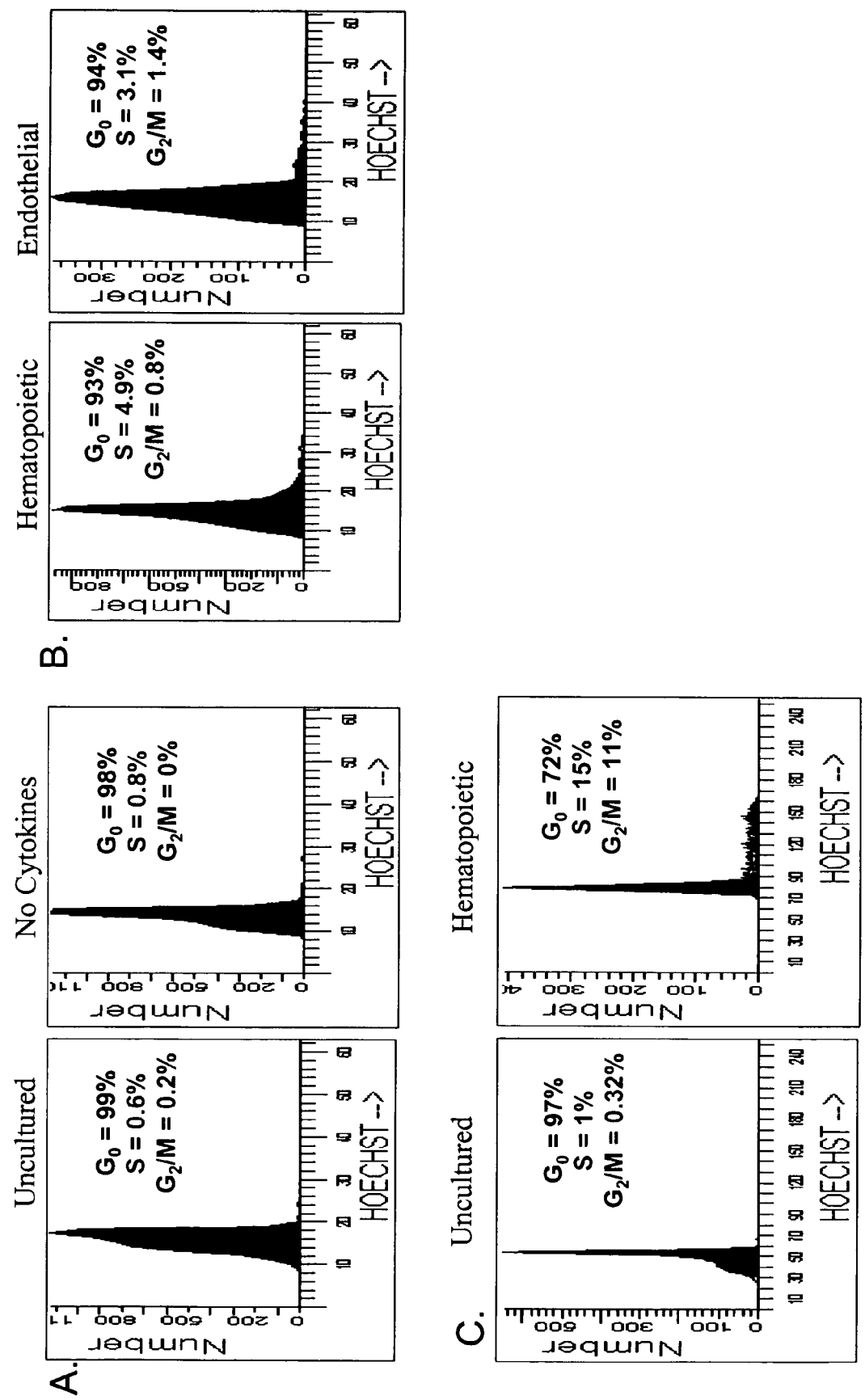
FIG. 9 illustrates a cell cycle analysis in cultured purified CD133+ cells. The CD133+ cells were purified and analyzed for cell cycle stages (A) immediately; (B) cultured for 24 hours under hematopoietic-driving or endothelial-driving conditions; or (C) cultured for 72 hours under hematopoietic-driving conditions. Cells were fixed, permeabilized, the DNA stained with Hoechst, and analyzed for cell cycle stages.

The results are illustrated in FIG. 9. The analysis of cell cycle stages of freshly isolated CD133+ cells (A) showed that 99% of the cells were resting in $G_0$ phase. After 24 hours of culture in cytokines (B), no significant cell division was found in hematopoietic or endothelial conditions, with the majority of the cells (93%-94%) still in $G_0$ phase at that time. After 72 hours in hematopoietic conditions, however, 15% of the cells were in S-phase and 11% of the cells were in $G_2$/M-phase. This data shows that differential protein expression, discussed above, after only 24 hours of incubation in specific cytokines, was progressing along differential gene expression programs, although very little cell division had taken place at that time. Therefore, with no cellular division having occurred at 24 hours, cells cultured in hematopoietic or endothelial conditions are still, in effect, the same cells as originally plated.

Example 5

Figure 10:
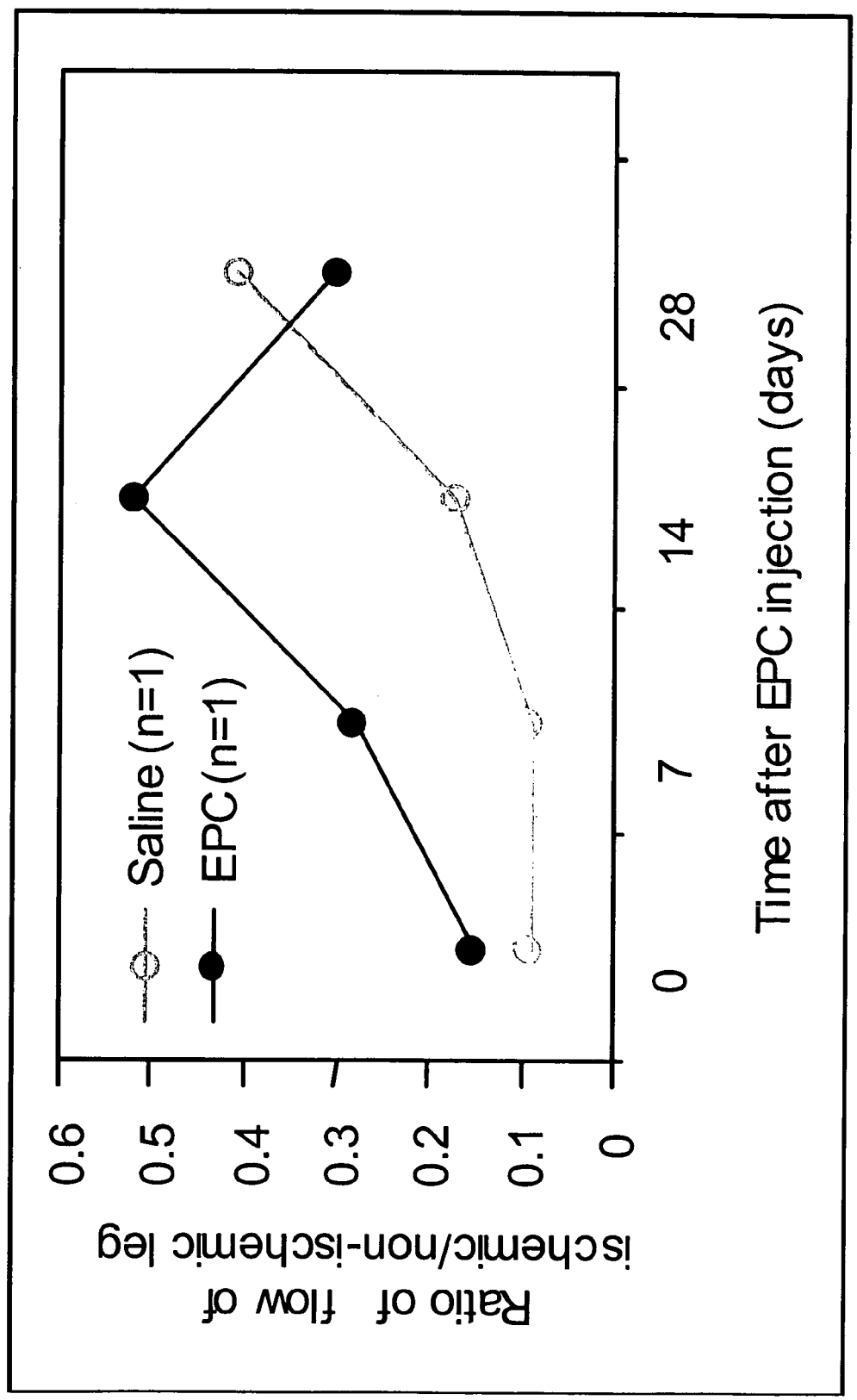
FIG. 10 depicts neovascularization by EPC derived from purified CD133+ cells in the mouse hindlimb ischemia model. Blood flow was measured over time by Laser Doppler and expressed as the ratio between the ischemic and non-ischemic leg.

Neovascularization in the Mouse Hind-Limb Injury Model by EPC Derived from Purified UCB CD133+ Cells CD133+ were selected as described in Example 3. After selection, the cells were seeded at 50,000-70,000 cells/well in 96-well plates under the same endothelial-driving culture conditions as described in Example 4. After 7 days of culture, cells were injected intracardially into mice that had undergone hind-limb femoral artery ligation by the method described in Example 2. Cell yields ranged from 58-130% of plated CD133+ cells, or 0.26% of the initial number of MNC. Blood flow was measured by laser Doppler flowmeter over time, and the results illustrated in FIG. 10 are expressed as the ratio between the blood flow in the injured and the uninjured leg over time. The results show increased blood flow in the mouse receiving CD133+ cells 14 days after surgery, when compared to the saline control injected on the same day. Analyses at a later time point (day 28) were notable for a significant improvement in the Doppler flow measurements in control mice injected with saline alone.

Example 6

Human Mesenchymal Stem Cells and Human Umbilical Vein Endothelial Cells Reciprocally Induce Mitotic Expansion Early angiogenic interactions between cells that are not in physical contact are mediated by soluble factors. Human mesenchymal stem cells secrete factors to support developmental processes such as osteogenesis, hematopoiesis and osteoclastogenesis. Many of the cytokines that modulate these processes also affect endothelial cell growth. The following examples illustrate that hMSCs secrete proteins that stimulate growth of mature endothelial cells. The examples also illustrate that soluble factors derived from mature endothelial cells stimulate the growth of hMSCs.

1) Human Bone Marrow-Derived Mesenchymal Stem Cells (hMSC): Isolation and Culture-Expansion Bone marrow was aspirated from the iliac crests of six human donors. Human mesenchymal stem cells were purified and cultured by a modification of previous reported methods (Haynesworth, S E et al. 1992. Bone 13, 81-88). Briefly, bone marrow aspirates were transferred from 20 ml. syringes into 50 ml conical tubes containing 25 ml of growth medium. Growth medium consisted of Dulbecco's Modified Eagles' Medium supplemented to 10% (v/v) with fetal bovine serum (FBS, GIBCO, Gaithersburg, Md.) from screened and selected lots. The tubes were spun in a Beckman table-top centrifuge at 1,200 rpm in a GS-6 swinging bucket rotor for 5 minutes to pellet the cells. The fat layer and supernatant were aspirated with a serological pipette and discarded. Cell pellets were resuspended to a volume of 5 ml with growth medium and then transferred to the top of preformed 35 ml gradients of 70% Percoll. The samples were loaded into a Sorvall SS-34 fixed angle rotor and centrifuged in a Sorvall High Speed Centrifuge at 460 g for 15 minutes. The low density fraction of approximately 12 ml (pooled density=1.03 g/ml) was collected from each gradient and transferred to 50 ml conical tubes to each of which was added 30 ml of growth medium. The tubes were centrifuged at 1,200 rpm to pellet the cells. The supernatants were discarded and the cells were resuspended in 20 ml of growth medium and counted with a hemocytometer after lysing red blood cells with 4% acetic acid. Cells were adjusted to a concentration of $5 \times 10^7$ cells per 7 ml and seeded onto 100 mm culture plates at 7 ml per plate.

The cells were cultured in growth medium at 37° C. in a humidified atmosphere containing 95% air and 5% $CO_2$, with medium changes every 3-4 days. When primary culture dishes became nearly confluent at 10-14 days, the cells were detached with 0.25% (w/v) trypsin containing 1 mM EDTA for 5 min at 37° C. The enzymatic activity of trypsin was stopped by adding ½ volume of calf serum. The cells were counted and resuspended in growth medium. Cell yield was about 0.26% of the initial number of MNC.

2) Conditioned Medium Growth Assays

Human mesenchymal stem cells, obtained as in Example 6 Part I, or human umbilical vein endothelial cells (HUVECs) were plated in 35 mm dishes and allowed to attach in growth medium. Following attachment, the cells were washed and then incubated for 12 hours in serum-free (HMSC) or low serum (HUVEC) medium to reduce residual serum proteins that might remain in the cytoplasm of the cells and synchronize growth phase of these cells. The cells were washed again before they were incubated for 72 hours (hMSCs) or 48 hours (HUVECs) in various concentrations of conditioned medium. Cells were quantified by hemocytometer.

To generate hMSC conditioned medium, hMSC at 75% confluence in 100 mm plates were washed and incubated in serum-free Dulbecco's Modified Eagles' Medium with low glucose (DMEM-LG) for 24 hours. The hMSCs were washed with Tyrode's balanced salt solution and then incubated to condition a serum-free defined medium (80% Iscove's, 12% DMEM-LG, and 8% chick fibroblast basal medium MCDB 201) for 72 hours. After the conditioning period, the medium was removed and centrifuged to remove cellular debris. The cells that conditioned the medium were quantified and conditioned medium was normalized to the cell number by dilution with serum-free defined medium to 10,000 cells/ml.

Conditioned medium was concentrated to 20× using Centricon 3 KDa molecular weight (MW) cut-off centrifugal devices in a Sorvall centrifuge at 4° C. Concentrated conditioned medium and filtrate (flow-through from concentration units containing no protein over 3 KDa MW) were either used immediately or stored at −20° C. The filtrate was centrifuged to remove cellular debris and then used to dilute the 20× conditioned medium to 2× (twice the final concentration). To produce 1× conditioned medium, fresh serum-free medium was added at a 1:1 ratio to provide essential nutrients.

HUVEC-conditioned medium was prepared as described above for hMSC conditioned medium, except that the HUVECs were grown in Medium 199 with 1% FBS for 48 hours. After concentration, the HUVEC-conditioned medium was diluted to 2× with flow through filtrate, as described above. The conditioned medium was then diluted to 1× with fresh Medium 199 with 1% FBS.

3) Effect of Conditioned Medium on Mitotic Expansion of hMSCs or HUVECs

Figure 11:
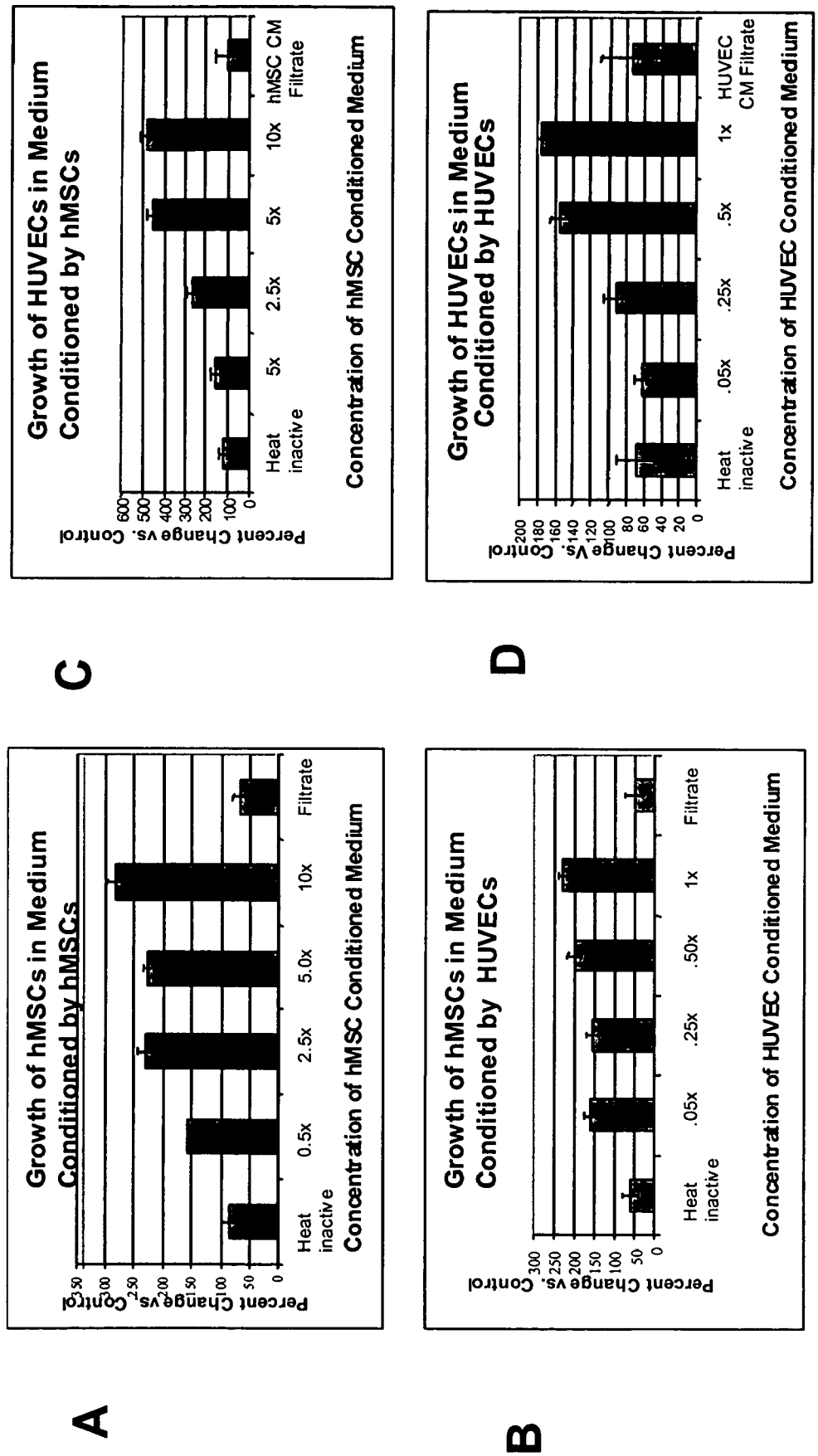
FIG. 11 illustrates the dose response mitotic expansion of human mesenchymal stem cell (hMSC) number following incubation in medium conditioned by human umbilical vein endothelial cells (HUVECs) (B), and the dose response mitotic expansion of HUVEC cell number following incubation in medium conditioned by hMSCs (C). (A) and (D) are control growth cultures.

FIG. 11 illustrates the dose response mitotic expansion of hMSC cell number following incubation in medium conditioned by HUVECs (B), and the dose response mitotic expansion of HUVEC cell number following incubation in medium conditioned by hMSCs (C), respectively. The growth stimulatory effect by the conditioned medium (CM) was not evident with conditioned medium that had been heat inactivated by boiling. Filtrates (flow through from concentration units with a 3 KDa MW cut-off) did not have a stimulatory effect for either cell type.

Control medium in all figures was combined unconditioned medium at a 1:1 ratio with fresh minimal medium best suited for the cell type. HUVEC 1× control medium contains 1% FBS. Dilutions of HUVEC control medium contain proportionately less FBS but do not vary by more than 1% FBS. FIGS. 11(A) and 11(D) are control growth cultures.

Example 7

Chemotactic Migration of hMSCs and HUVECs Toward Secreted Factors in Conditioned Medium.

Tissues acquire new vasculature, in part, through the release of factors that induce the chemotactic migration of endothelial cells from existing blood vessels into the tissue. Likewise, newly formed vasculature matures and stabilizes, in part, as a result of their interaction with mesenchymal pericytes that migrate to the site of the new vessel in response to chemotactic factors released by the endothelial cells. The following example illustrates that hMSCs can stimulate endothelial cell migration and serve as pericyte precursors, and respond to chemotactic factors released by endothelial cells. Boyden chambers were used to measure the migration of hMSCs and HUVECs in response to chemotactic factors secreted into the conditioned medium of the other.

1) Chemotactic Migration Toward Conditioned Medium in Boyden Chambers

Lower wells of Neuroprobe 48-well Boyden chambers were loaded with varying concentrations either the hMSC- or HUVEC conditioned medium described in Example 6. A 1% gelatin coated polycarbonate membrane with 5 µm pores was placed on top of the lower wells and the chamber was assembled. hMSCs or HUVECs were pelleted and washed thoroughly before they were suspended in either serum-free (for dose response assays) or varying concentrations of conditioned medium (checkerboard assays). hMSC or HUVEC cell suspensions were loaded in the upper wells. The chambers were incubated at 37° C. for 5 hours to permit migration of cells from the upper well, through the membrane, into conditioned medium in the lower wells. Following the 5 hour incubation, the chambers were disassembled and the membrane was removed. Cells were scraped from the upper surface of the membrane leaving only cells that migrated through the membrane pores. The migratory cells were then fixed in formaldehyde, stained with crystal violet, and mounted on slides. Slides were scanned for dose response and quantified by direct cell count using an Olympus 480E microscope. A row of three dots on the filter represents migration of cells in three wells of a given condition.

Figure 12:
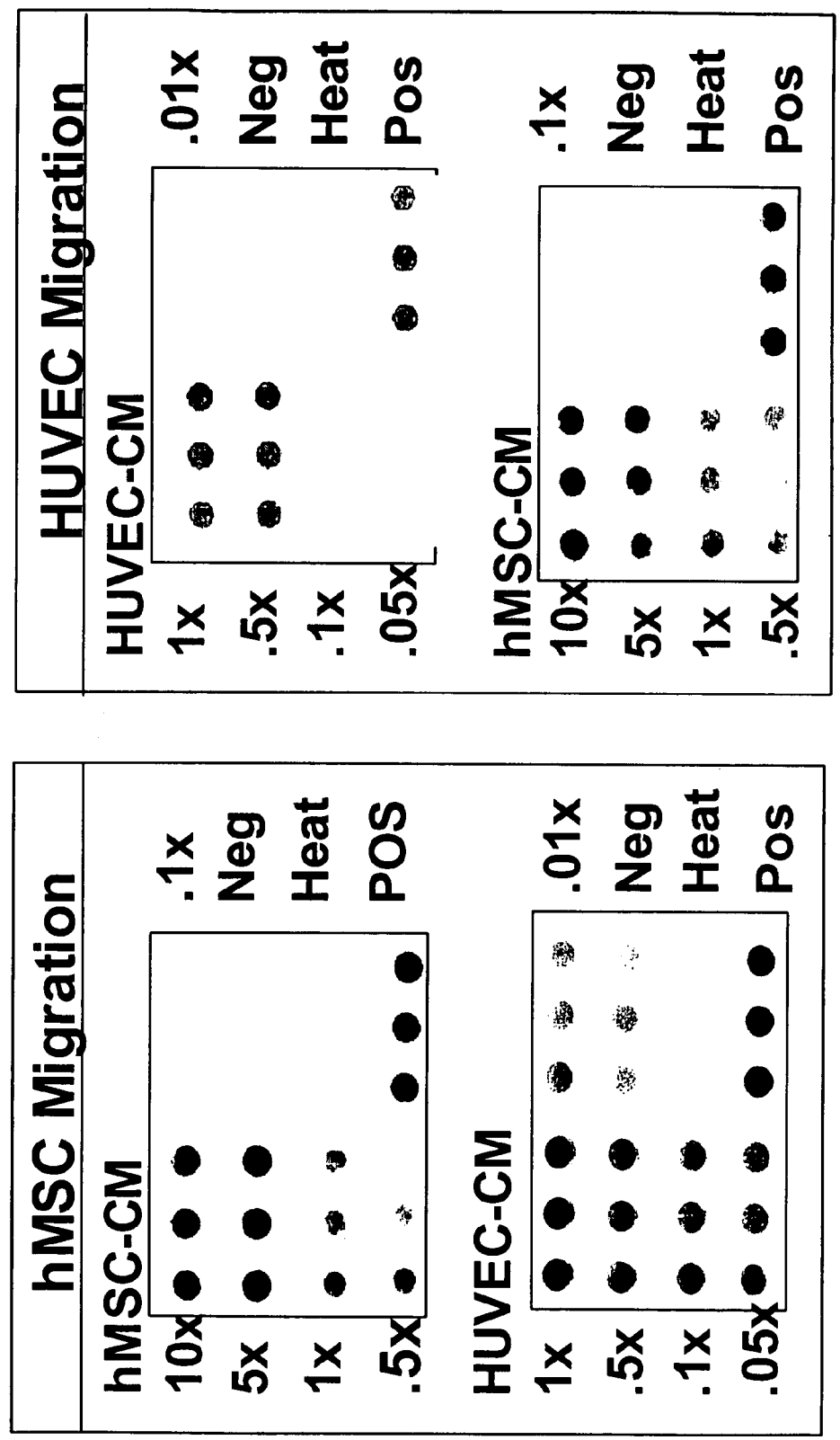
FIG. 12 illustrates migration of hMSCs (top) and HUVECs (bottom) toward hMSC-conditioned medium (left) and migration of HUVECs (top) and hMSCs (bottom) toward HUVEC-conditioned medium (right).

FIG. 12 illustrates migration of hMSCs (top) and HUVECs (bottom) toward hMSC-conditioned medium (left panel), and migration of HUVECs (top) and hMSCs (bottom) toward HUVEC-conditioned medium (right panel). For both cell types, the greatest migration is observed in the three spots on the upper left hand corner of the membrane that correspond with the highest concentration (10×) of hMSC- or HUVEC-conditioned medium, respectively. The intensity of the spots (that directly corresponds to the number of cells attached to the membrane) decreases as the concentration of conditioned medium decreases, thus demonstrating a dose dependent migration of both hMSCs and HUVECs toward HUVEC- or hMSC-conditioned medium, respectively. Heat denatured conditioned medium showed migration patterns similar to the negative control. 10% FBS was used as a positive control.

Example 8

Human Mesenchymal Stem Cells Express Vascular Endothelial Growth Factor (VEGF) Genes and VEGF Receptor Genes.

VEGFs have been described as endothelial cell-specific ligands with receptors found exclusively on endothelial cells. However, recent reports demonstrate expression of VEGF receptors on non-endothelial cells including human bone marrow stromal cells. The following two examples demonstrate that hMSCs also express VEGF growth factors and receptors.

1) RT-PCR Analysis of the Expression of VEGF Family of Growth Factors mRNA by hMSC.

RT-PCR was used to show messenger RNA expression of VEGF family growth factor genes. Qiagen kits were used to generate total RNA from pelleted hMSCs. A cDNA synthesis kit (Amersham) generated cDNA from total RNA. cDNA was combined with specific primers for VEGF family genes (VEGF-A, -B, -C, -D, and PlGF) and added to RT-PCR Ready-To-Go beads for amplification in a Robocycler 480 PCR machine. All reactions employed the same 35 cycle amplification program with optimal annealing temperatures set for the specific primer.

2) Visualization of VEGF PCR Products

Figure 13:
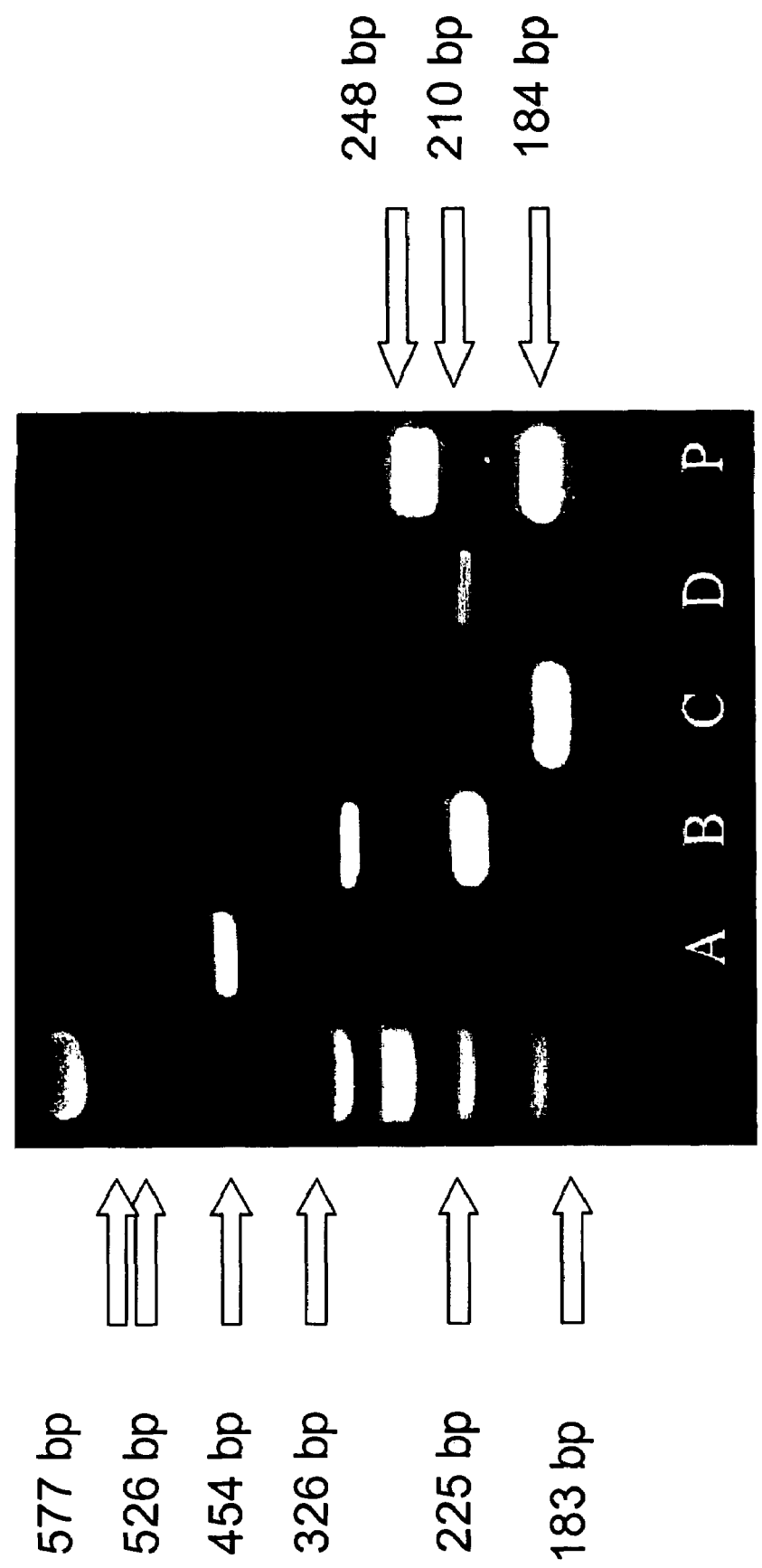
FIG. 13 illustrates that hMSCs express vascular endothelial growth factor (VEGF) genes. The expression of VEGF family growth factor mRNA was determined using RT-PCR. Specific primers were added to cDNA to amplify VEGF family genes over 35 cycles. Varying amounts of PCR product were run on a 2% agarose gel and visualized using ethidium bromide staining. The size of the PCR products are as follows: VEGF-A at 577 bp, 526 bp, and 454 bp; VEGF-B at 326 bp and 225 bp; VEGF-C at 183 bp; VEGF-D at 225 bp; and PIGF at 248 bp and 184 bp.

Varying amounts of PCR product were run on a 2% agarose gel and visualized using ethidium bromide staining. FIG. 13 illustrates the sizes of the isolated PCR products, as follows: VEGF-A at 577 bp, 526 bp, and 454 bp; VEGF-B at 326 bp and 225 bp; VEGF-C at 183 bp; VEGF-D at 225 bp; and PlGF at 248 bp and 184 bp.

3) RT-PCR Analysis of VEGF Receptor Expression by hMSC

RT-PCR analysis was performed as described in Example 9 using specific primers for VEGF receptors 1, 2 and 3, as well as Neuropilin-1 and Neuropilin-2.

4) Visualization of VEGF PCR Receptor Products

Figure 14:
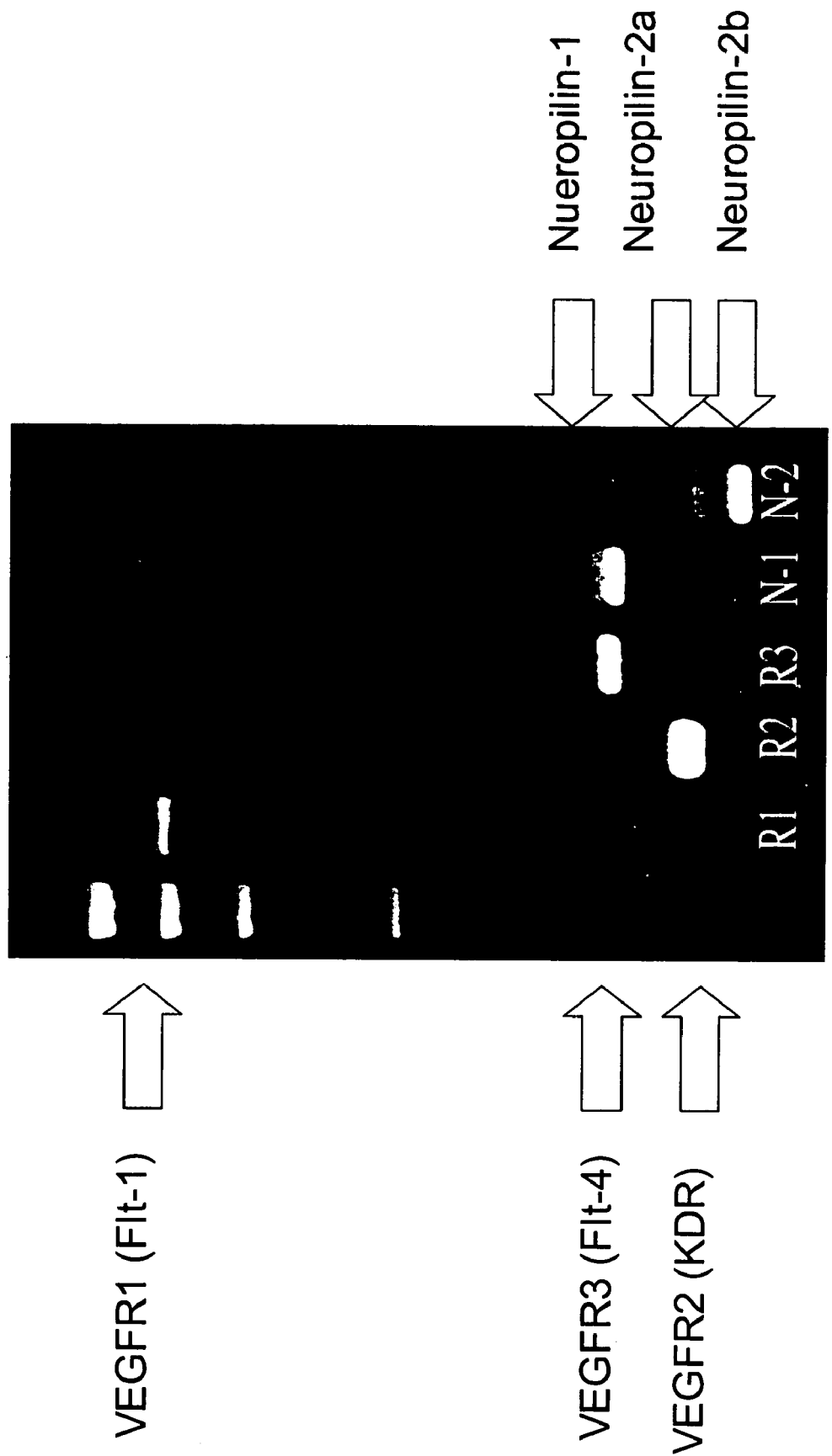
FIG. 14 illustrates VEGF receptor mRNA expression by hMSCs. Total RNA was added to specific primers to amplify VEGF receptor genes by RT-PCR. Varying amounts of PCR product were run on a 2% agarose gel and visualized using ethidium bromide staining. Shown are high molecular weight DNA markers, VEGFR1 (1,098 bp); VEGFR2 (326 bp); VEGFR3 (380 bp); Neuropilin-1 (375 bp) and Neuropilin-2 (304 bp and 289 bp).
Figure 16B:
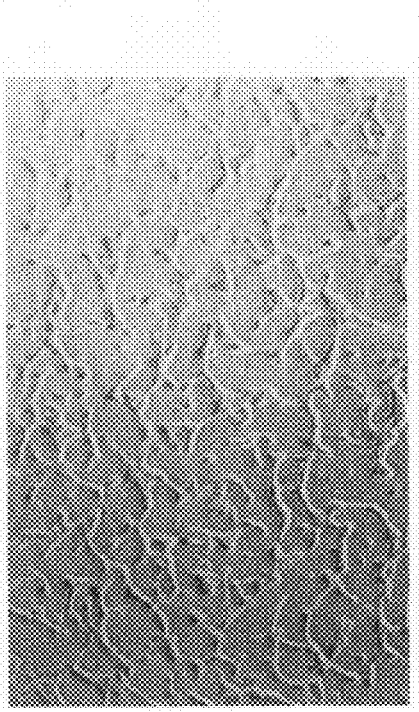
FIG. 16 illustrates that hMSCs selectively migrate to endothelial tube-like structures. HUVECs in monoculture (A) were induced to form tube-like structures by addition of Vitrogen gel (B). DiI stained hMSCs were added to the top of the gel cultures (C). 24 hours later, the hMSCs are located along endothelial cell tube-like structures (D).
Figure 16D:
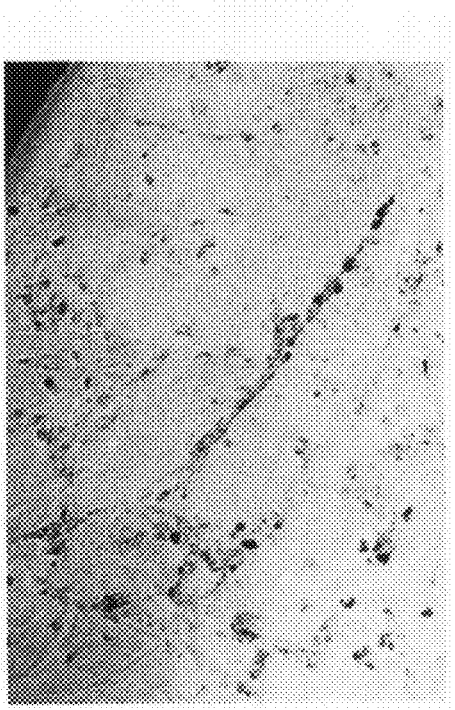
Figure 16A:
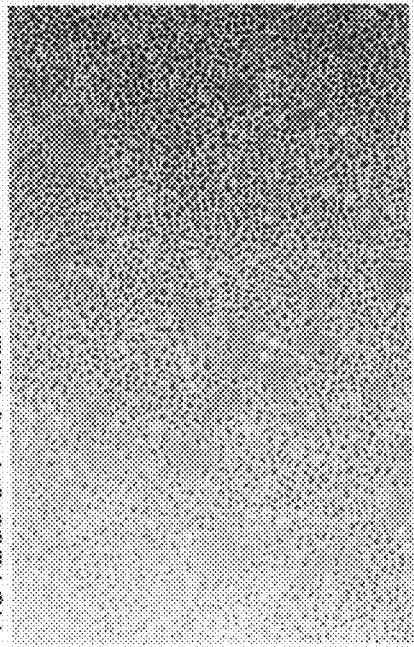
Figure 16C:
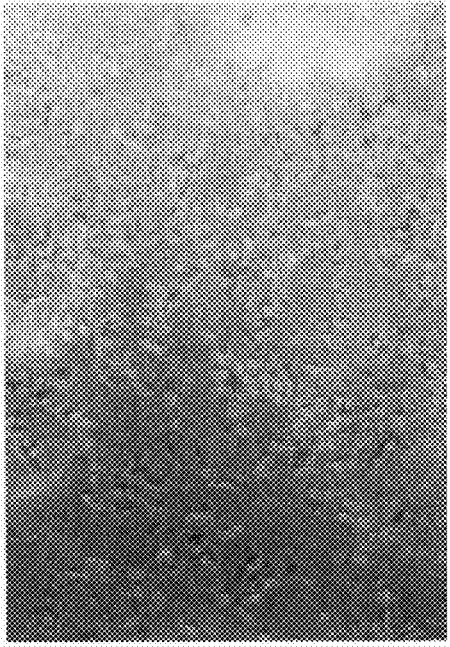

The visualization was carried out as described above. FIG. 14 illustrates high molecular weight DNA markers, VEGFR1

(1,098 bp), VEGFR2 (326 bp), VEGFR3 (380 bp); Neuropilin-1 (375 bp) and Neuropilin-2 (304 bp and 289 bp).

Example 9

Direct cell contact between pericyte precursors and endothelial cells leads to interactions that activate TGF-β1, which ends the angiogenic growth phase and induces vascular differentiation of each cell type. TGF-β1 is secreted in a latent form by most cells in culture. The physiological relevance of TGF-β1 is the regulation of its activation. There are no reports in the literature of production of active TGF-β1 in non-transformed cells in monoculture. However, co-cultures of endothelial cells with a multipotent murine fibroblast (10T½ cells), pericytes, or smooth muscle cells in co-culture with endothelial cells, have been shown to activate latent TGF-β1 through a mechanism involving proteolytic cleavage of a latency peptide by plasmin. This example illustrates that hMSCs interact with endothelial cells through direct cell contact and activate the key anti-angiogenic factor, TGF-β1.

ELISA analysis was employed to detect active TGF-β1 protein in conditioned medium from hMSC and HUVEC monocultures or co-cultures, prepared as described in Example 6, above.

FIG. 15(A) demonstrates secretion of latent TGF-β1 by hMSCs and endothelial cells in monoculture. As expected, no active TGF-β1 was measurable in conditioned medium from HMSC or HUVECs in monoculture. FIG. 15(B) demonstrates that active TGF-β1 was not produced in monocultures of hMSCs or HUVECs but was measured in co-cultures of the same cells.

Example 10 hMSCs Selectively Migrate to Endothelial Tube-like Structures.

Evidence suggests that endothelial cell tubes recruit surrounding mesenchymal cells to migrate towards and co-localize with newly forming vessels to stabilize them. Endothelial cell tubes in 3-dimensional type I collagen gels are an in vitro correlate of newly formed vessels. The data presented in the examples above demonstrate that hMSCs and HUVECs interact through secreted proteins that induce chemotactic migration. Further, the data demonstrate that hMSCs interact with HUVECs in co-culture and modulate signaling to activate TGF-β1, an anti-angiogenic factor that has been shown to end the angiogenic growth phase and induce terminal differentiation of certain fibroblasts and endothelial cells.

This example demonstrates that hMSCs can be induced to migrate to endothelial cell tube-like structures, co-localize, and differentiate into pericytes.

1) Preparation of Tube-Like Structures and Visualization of hMSC Migration

Briefly, DiI stained hMSCs were added to Vitrogen (type I collagen) 3D gel cultures of endothelial cell tube-like structures to investigate co-localization. DiI is a vital dye. To establish cultures of HUVEC tube-like structures, HUVECs were plated at 300,000 cells/ml onto 1% gelatin coated 35 mm plates. Following attachment, endothelial growth medium was removed and cells were washed thoroughly with Tyrode's solution. A solution of Vitrogen gel at a 1:1 ratio with DMEM-LG with 10% FBS was added to the endothelial cells. Following solidification of the Vitrogen mixture, an additional 1 ml of endothelial growth medium was added and cultures were incubated overnight to permit tube-like structure formation.

To stain hMSCs with DiI, hMSCs were plated at 50,000 cells/ml in 35 mm plates. hMSCs were incubated overnight in DMEM-LG with 10% FBS to permit attachment. Cultures were then washed with Tyrode's solution and incubated for 6 hours in DMEM-LG with 10% FBS combined with 1 μg/ml DiI. Following the incubation, hMSCs were washed thoroughly and then trypsinized to remove cells from the plate. The hMSCs were pelleted by centrifugation and then resuspended at 30,000 cells/ml in DMEM-LG with 2% FBS.

One ml of hMSC suspension was added to the upper surface of HUVEC tube-like structures in gel culture. Co-localization required migration of hMSCs through the 3D gel to tube-like structures located near the bottom surfaces. Cultures were monitored and photographed.

The results are illustrated in FIG. 16. In panel A, HUVECs are shown in a typical 2-dimensional culture. Panel B shows the tube-like structures that formed 12 hours after Vitrogen 3D collagen gel was added to the cells in panel A. An extensive network plexus of endothelial tubes is visible. Panel C illustrates the DiI stained hMSCs randomly distributed across the surface of the 3D collagen gel. Panel D shows the same culture 24 hours after addition of the hMSCs to the HUVECS in the 3D collagen gel. The hMSCs migrated through the gel and selectively co-localized with the endothelial cell tubes. Results were reproducible using multiple hMSC and HUVEC donors in the same experimental conditions.

Example 11

Augmented Neovascularization in the Mouse Hind-Limb Injury Model by EPC Derived from Purified UCB CD133$^+$ Cells Supplemented with Human Mesenchymal Stem Cells (hMSC).

A series of experiments was performed to determine whether stromal elements (e.g., hMSC) added to UCB-derived EPC would augment neovascularization in the mouse hind-limb ischemia model.

1) Isolation and Culture Expansion of hMSCs hMSCs from adult human bone marrow were isolated and expanded in culture as described in Example 6.

2) Isolation and Culture Expansion of CD133$^+$ Cells from UCB

CD133$^+$ from UCB were selected as described in Example 3. After selection, the cells were seeded at 50,000-70,000 cells/well in 96 well plates under the same endothelial-driving culture conditions as described in Example 4. Cell yields ranged from 58-130% of plated CD133$^+$ cells 3) Neovascularization in the Mouse Hind-Limb Injury Model by EPC Derived from Purified UCB CD133$^+$ Cells Supplemented with hMSCs.

Figure 17:
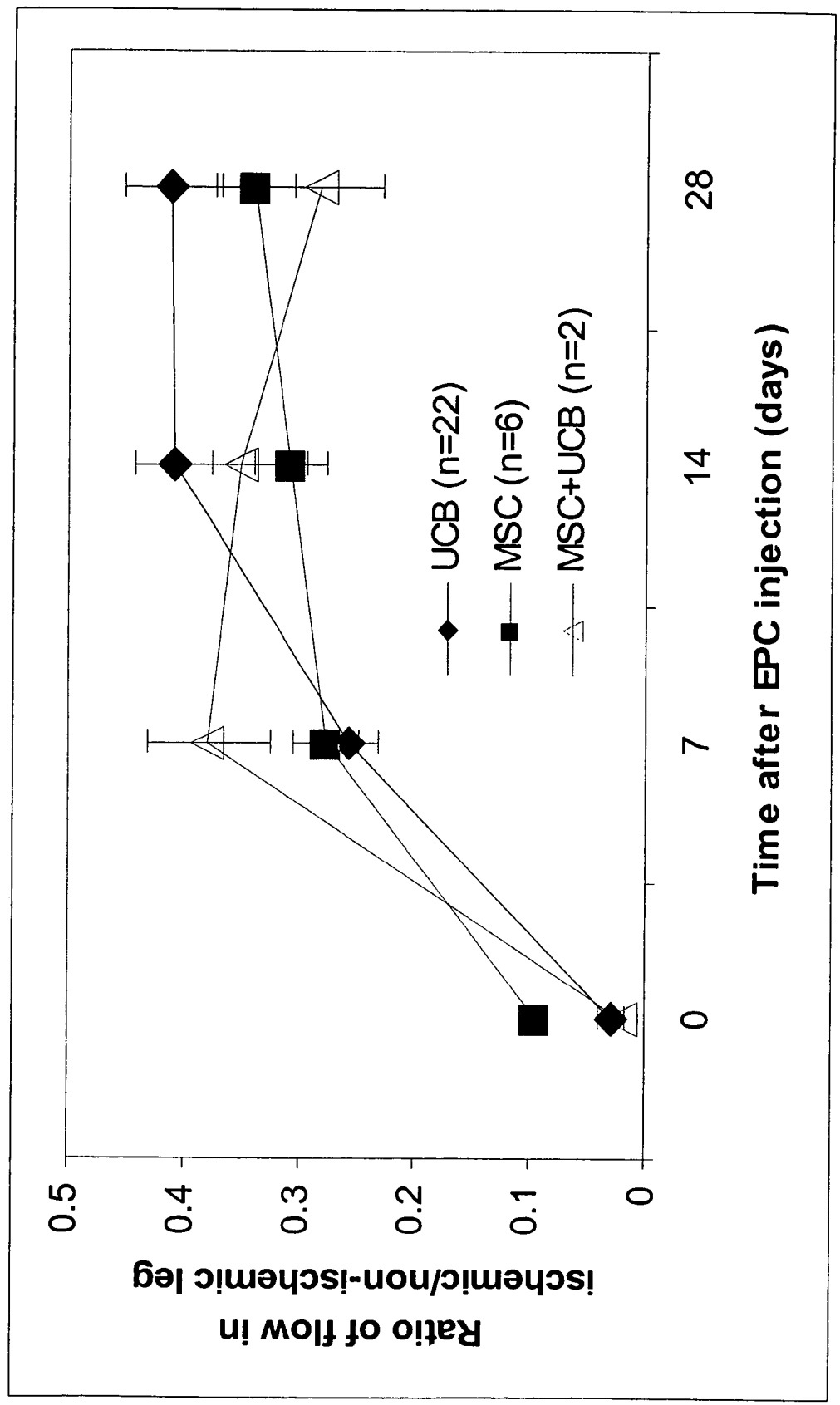
FIG. 17 depicts neovascularization by purified CD133$^+$ cells derived from UCB and a combination of CD133$^+$ cells+ hMSC in the mouse hindlimb ischemia model. Blood flow was measured over time by Laser Doppler and expressed as the ratio between the ischemic and non-ischemic leg. The results in a small number of mice indicates increased blood flow in the mice receiving both CD133$^+$ cells and hMSC at day 7 after surgery, compared with mice infused with CD133$^+$ cells alone (day 14).

After 7 days of culture, $1 \times 10^6$ CD133$^+$ cells and $1 \times 10^6$ hMSC were co-injected intracardially into mice that had undergone hind-limb femoral artery ligation by the method described in Example 2. Blood flow was measured by laser Doppler flowmeter over time, and the results illustrated in FIG. 17 are expressed as the ratio between the blood flow in the injured and the uninjured leg over time. The results show increased blood flow in the mouse receiving both CD133$^+$ cells and hMSC cells at day 7 after surgery compared with mice infused with CD133$^+$ cells (day 14) or hMSC alone. This result suggests that improved blood flow was achieved at an earlier time point (day 7) after co-infusion of hMSC with CD133$^+$ cells. However, because of the small number of mice studied in the co-infusion experiment, there is not sufficient data to generate appropriate statistical analysis. The augmentation effect of concurrent hMSC infusion did not persist at later time points.

Example 12

Intracoronary Infusion of UCB-Derived CD133$^+$ Cells in Patients with Chronic Coronary Ischemia.

A patient with chronic coronary ischemia, having an area of documented ischemic but viable myocardium supplied by epicardial vessels that provide collateral flow in the distribution of a chronic totally occluded vessel, is eligible for treatment. The eligible patient must report past experience with class II-IV angina as defined by the Canadian Cardiovascular Society. The patient is screened within 30 days of scheduling of a percutaneous coronary intervention (PCI, e.g., balloon angioplasty, stenting, atherotomy, or rotational atherectomy). Areas of ischemic but viable myocardium are identified by exercise/pharmacologic nuclear stress testing in addition to PET scanning. Echocardiographic evaluation of left ventricular ejection fraction (>45% required for patient eligibility) and regional wall motion is part of the initial screening along with complete history and physical examination including a review of concomitant medications, ECG, and baseline laboratory panels (CBC, basic metabolic profile, coagulation panel and acute myocardial infarction panel). Coronary angiography is evaluated for anatomy favorable for the treatment protocol, i.e., chronic total occlusion of an epicardial artery with distal distribution supplied by well established collaterals with a separate culprit vessel amenable to PCI.

Patients ineligible for stem cell treatment include those having coronary lesions amenable to PCI including brachytherapy, contraindications for PCI, cardiac catheterization, bone marrow aspiration, as well as those having had a myocardial infarction within the previous three months, having documented bleeding diathesis, having a known malignancy involving the hematopoietic/lymphoid system, having baseline ECG abnormalities that would hinder interpretation of baseline ECG for ischemia, having severe co-morbidities including renal failure, or having anticipated unavailability for follow-up visits secondary to psychological or social reasons.

Once coronary anatomy in the eligible patient is determined, the patient is removed from the catheterization laboratory and undergoes bone marrow aspiration under conscious sedation. Approximately 150-250 ml of bone marrow aspirate is removed from the iliac crest. Multiple puncture sites may be needed to obtain the desired volume. This volume of bone marrow aspirate yields approximately $10^6$ MNCs.

CD133$^+$ cells are isolated from the MNCs according to the method described in Example 3, by labeling with CD133$^+$-conjugated magnetic beads followed by automated sorting through magnetic columns (Automacs, Miltenyi). The selected CD133$^+$ cells are then washed in buffer solution and can be stored in a concentrated solution of 5 ml. normal saline.

After the patient is given time to recover from the bone marrow aspiration, a PCI is performed. When the operating interventional cardiologist has determined that the PCI is successful, the patient is observed for approximately 5 minutes for any complications. If none, transplantation of stem cells is completed at the same sitting. Approximately $1\times10^4$ to $1\times10^5$ of the isolated CD133$^+$ cells are infused via an infusion catheter into the epicardial vessel supplying the majority of collaterals vessels to the chronically ischemic zone. The epicardial coronary artery, which is the source of collateral vessels to the viable myocardium formerly supplied by a vessel which is now totally occluded, is identified by fluoroscopy. Equipment is passed through an introducer sheath placed in a peripheral vessel for the index PCI. The target parent vessel is cannulated with an infusion catheter through a guide catheter that is placed in the ostium of the appropriate coronary artery in the sinus of Valsalva. The CD133$^+$ cells in a 5 ml solution of normal saline are infused by manual injection over 3 minutes. An additional 2 ml of normal saline is infused through the catheter immediately after the stem cell solution in order to prevent residual cells from accumulating in the catheter proper.

At the end of the stem cell infusion, a selected coronary angiogram of the vessel is performed to assess TIMI flow and evaluate the integrity of the vessel wall. The patient is monitored in the cardiac catheterization laboratory for 5 minutes post procedure for any complications.

The patient is then observed in a monitored setting for 24 hours after the procedure, with an ECG and cardiac enzyme analysis obtained at 8, 16 and 24 hours.

Clinical follow-up evaluation of the patient is performed thereafter at 7, 30, 90, 180 and 365 days. The success of the PCI and stem cell infusion treatment is measured by an improvement in exercise capacity (e.g., total exercise duration in seconds, change in exercise duration, time to onset of angina, time to 1 mm ST depression, and the like); major cardiac events (e.g., death, revascularization, readmission to hospital secondary to angina, myocardial infarction, and the like); myocardial infarction within 24 hours post procedure or later than 24 hours post procedure (e.g., as measured by an elevation of cardiac enzymes, ECG changes, chest pain not relieved by nitroglycerine, and the like); improvement in anginal symptoms; length of secondary hospital stay; decrease in medication usage; subjective improvement in angina; improvement in left ventricular function and ejection fraction as measured by 2D echocardiogram; improvement in the total area of ischemia compared to initial screening test by nuclear stress testing; and improvement in the viable zone of myocardium compared to initial screening test by PET scan.

Example 13

Intracoronary Infusion of UCB-Derived CD133$^+$ Cells and Bone Marrow-Derived hMSC Cells to Patients with Chronic Coronary Ischemia.

A patient is selected and monitored according to the protocol described in Example 12. Once coronary anatomy in the eligible patient is determined, the patient is removed from the catheterization laboratory and undergoes bone marrow aspiration under conscious sedation. Approximately 150-250 ml of bone marrow aspirate is removed from the iliac crest.

Autologous hMSCs are isolated from the bone marrow aspirate according to the method described in Example 6. The yield of hMSC is approximately 1/10,000 to 1/100,000 MNC. Therefore, approximately 300-3,000 hMSC are obtained from 150-250 ml of bone marrow. After about 14 days of culture, the yield of hMSCs is approximately $10^4$ to $10^5$ with a purity of cells identified by the monoclonal antibody SH2 of 99% or greater. The hMSCs are washed in buffer solution and can be stored in a concentrated solution of 5 ml normal saline.

CD133$^+$ cells are isolated from umbilical cord blood according to the method described in Example 3, by labeling with CD133$^+$-conjugated magnetic beads followed by automated sorting through magnetic columns (Automacs, Miltenyi). The selected CD133$^+$ cells are then washed in buffer solution and can be stored in a concentrated solution of 5 ml. normal saline. The CD133$^+$ cells can be expanded in culture according to the method described in Example 12, if desired.

When hMSCs and CD133$^+$ cells are available for transplantation, a PCI is performed on the patient. When the operating interventional cardiologist has determined that the PCI is successful, the patient is observed for approximately 5 minutes for any complications. If none, transplantation of stem cells is completed at the same sitting. Approximately $1\times10^4$ to $1\times10^5$ of the isolated UCB-derived CD133$^+$ cells are infused in a 1:1 ratio with the autologous hMSCs via an infusion catheter into the epicardial vessel supplying the majority of collateral vessels to the chronically ischemic zone. The epicardial coronary artery, which is the source of collateral vessels to the viable myocardium formerly supplied by a vessel which is now totally occluded, is identified by fluoroscopy. Equipment is passed through an introducer sheath placed in a peripheral vessel for the index PCI. The target parent vessel is cannulated with an infusion catheter through a guide catheter that is placed in the ostium of the appropriate coronary artery in the sinus of Valsalva. The CD133$^+$ cells and autologous hMSC cells are co-infused in a 5 ml solution of normal saline by manual injection over 3 minutes. An additional 2 ml of normal saline is infused through the catheter immediately after the stem cell solution in order to prevent residual cells from accumulating in the catheter proper.

At the end of the stem cell infusion, the assessment and monitoring of the patient proceeds as described in Example 12.

Example 14

Recent studies have shown that intracoronary injections of progenitor mononuclear cells (MNC's) may be beneficial to patients that have suffered a myocardial infarction (Strauer B, et al. 2002. *Circulation,* 1913-1918; Assmus, B, et al. *Circulation* 2002; 106: 3009-3017. In these small trials, treatment patients received as much as 245 million cells via intracoronary injections of 3-3.5cc boluses of $25\times10^6$ cells/cc. No complications related to the cell injections were noted in either of these trials. Potential complications would include the possibility of inducing a myocardial infarction at the time of cell injection.

Theoretical consideration must be given to the possibility of inducing a thrombogenic state at the time of cell injections. The thrombogenic state could be secondary to the very nature of the cells or the slow coronary blood flow resulting from either hyperviscosity due to increased cell to plasma volume ratio or compromise of the microvascular environment. To date there are no studies to evaluate this potential serious complication. A small animal study was conducted designed to establish a safety threshold for intracoronary injections of autologus bone-marrow derived MNC's.

Yorkshire pigs weighing approximately 40-50 Kg were given intracoronary injections of autologus bone marrow derived MNC's in concentrations ranging from 1.5-5× $10^6$cells/cc plasma. The protocol was established to mimic the human clinical trial. The first (D1) or 25 second (D2) diagonal branch, see FIG. 1 below, was selected for cell injection based on size and ease of access using the intracoronary perfusion catheter. Coronary flow rate, measured as TIMI frame count, was noted before and after cell injections. The isolated mononuclear cells were injected over 1-2 minutes followed by a 1 cc intra-coronary saline flush.

The animals were followed for seven days and sacrificed after repeat coronary angiography. The hearts were removed pressure fixed with buffered normal saline with 10% formalin. The hearts were visually inspected for evidence of gross ischemia or infarction and then sent for histology.

Figure 18:
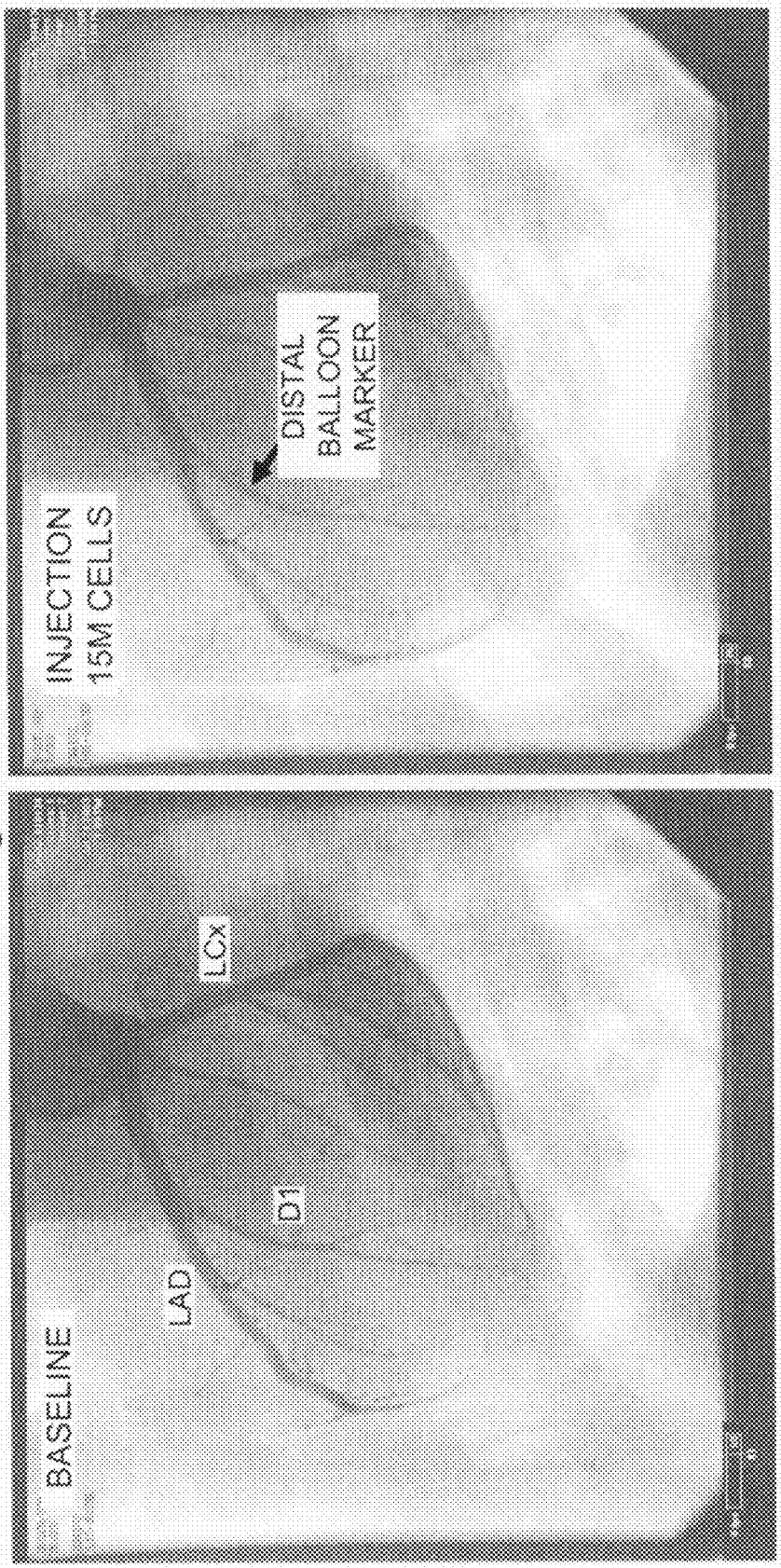
FIG. 18 shows still frame images of porcine angiograms, at baseline and after the injection of MNC's. LAD: Left Anterior Descending Artery, LCx: Left Circumflex artery, D1: first Diagonal branch.

Three pigs were tested for evidence of infraction. There was no evidence for myocardial infarction on gross inspection or on histology at any of the cell concentrations tested. At the highest concentration tested ($15\times10^6$ cells per 3 cc serum), there was a significant decrease in coronary flow (TIMI I) noted shortly after the cell infusion. The sluggish flow was noted in the LAD distribution as well as the targeted diagonal vessel (D1) (FIG. 18). The coronary flow recovered after approximately 10 minutes. There was no visual evidence of coronary spasm during or after the cell injection to explain the reduced flow.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

Example 15

Characterization of UCB-Derived CD133$^+$ Cells

Figure 19:
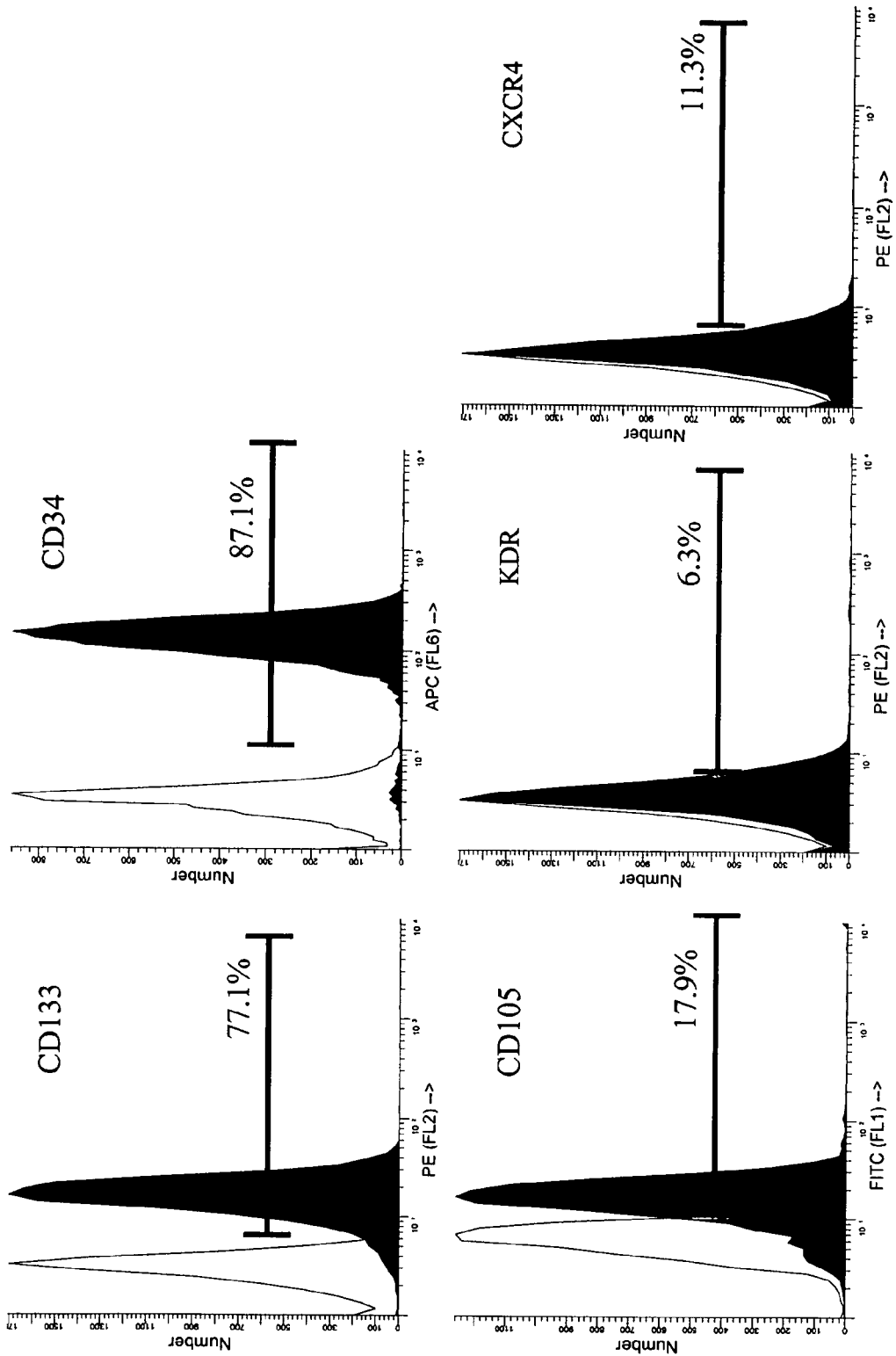
FIG. 19 describes the expression of cell surface markers, as determined by FACS sorting, of umbilical cord blood cells purified according to their expression of by the CD133 cell surface marker.
Figure 20:
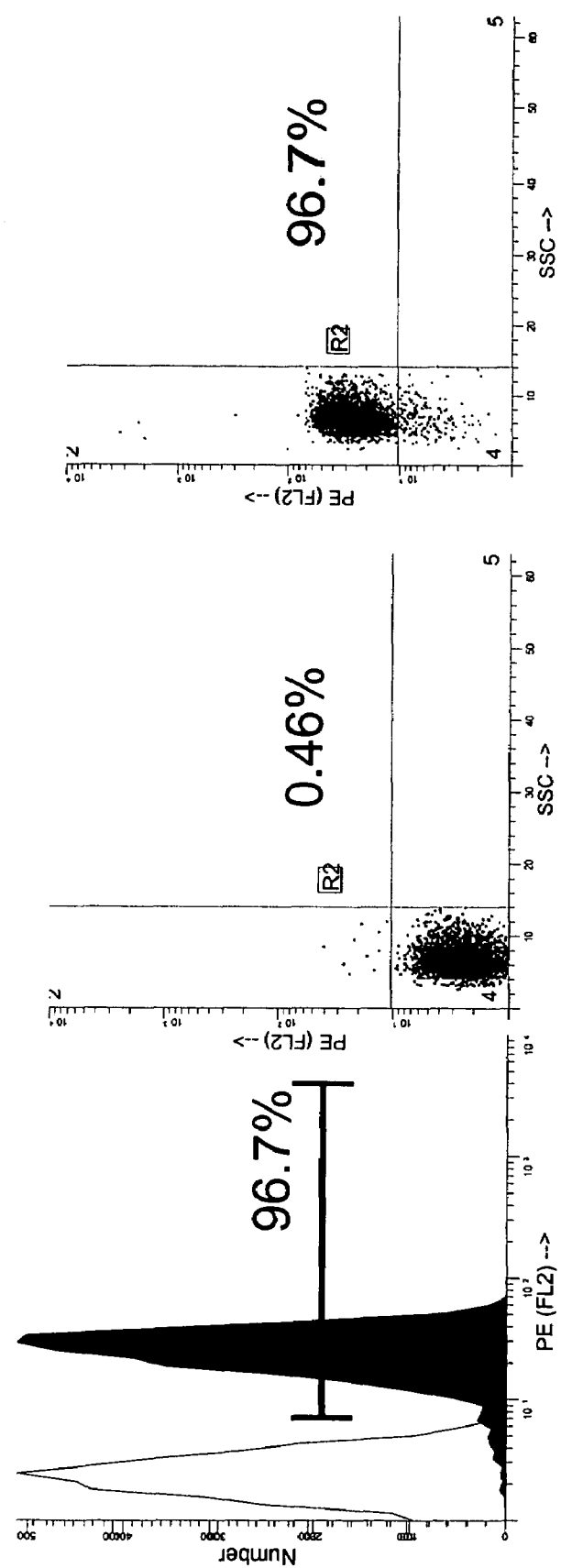
FIG. 20 describes the FACS sorting of CD133 cells from umbilical cord blood.

The CD133+ cells from Example 3 were further characterized to determine the surface expression of various markers. Mononuclear cells were isolated from UCB with density gradient centrifugation. CD133+ cells were isolated by magnetic separation (Miltenyi). Surface expression was evaluated by incubation for 20 minutes at 4° C. with fluorochrome-conjugated mAbs and appropriate isotype controls. An LSR flow cytometer (Coulter, Miami, Fla.) was used to acquire >5000 fluorescence events per sample. The results are shown in FIGS. 19 and 20 and in the following table:

| Marker | Cells expressing marker (% average) | SEM | Number of Samples |
|---|---|---|---|
| CD133 | 78.67 | 2.41 | 11 |
| CD34 | 87.42 | 3.11 | 10 |
| KDR (EGFR2) | 3.59 | 1.49 | 4 |
| CD105 | 22.74 | 2.84 | 3 |
| CXCR4 | 8.66 | 3.79 | 3 |

The following table shows the percentage of CD133+ cells expressing each of the five indicated markers for individual umbilical cord blood samples.

| Cord Sample | CD133 | CD34 | KDR | CD105 | CXCR4 |
|---|---|---|---|---|---|
| CB1144 + 133 | 75.26 | 81.78 | 4.03 | 27.73 | 13.51 |
| CB1230 + 133 | 62.83 | | | | |
| CB0174 + 133 | 72.31 | 76.11 | | | |
| CB1290 + 133 | 70.14 | 76.59 | | | |
| CB1299 + 133 | 89.6 | 99.1 | | | |
| CB1302 + 133 | 80.46 | 98.41 | 0.41 | 22.6 | 1.19 |
| CB0711 + 133 | 76.99 | 76.11 | | | |
| CB0996 + 133 | 85.27 | 92.88 | | | |
| CB1241 + 133 | 77.12 | 87.06 | 6.34 | 17.88 | 11.29 |
| CB1215 + 133 | 96.7 | 98.72 | 3.4 | | |
| Average | 78.67 | 87.42 | 3.55 | 22.74 | 8.66 |
| SEM | 3.11 | 3.37 | 1.09 | 2.46 | 3.28 |

We claim:

1. A method for improving blood flow to an ischemic myocardium having an area of viable myocardium in a subject in need thereof, comprising administering to said subject a therapeutically effective amount of enriched CD133$^+$/CD34$^+$/CXCR4$^-$ cells isolated from umbilical cord blood, wherein the enriched CD133$^+$/CD34$^+$/CXCR4$^-$ cells are administered by infusion into a coronary artery, wherein administering of the CD133$^+$/CD34$^+$/CXCR4$^-$ cells results in improved blood flow to said ischemic myocardium, wherein the CD133$^+$/CD34$^+$/CXCR4$^-$ cells are enriched from umbilical cord blood mononuclear cells at least two-fold prior to administration to the subject.

2. The method of claim 1, wherein the coronary artery is an epicardial vessel that provides collateral flow to said ischemic but viable myocardium in the distribution of a chronic partially or totally occluded vessel.

3. A method for improving blood flow to an ischemic myocardium having an area of viable myocardium in a subject in need thereof, comprising administering to said subject a therapeutically effective amount of a composition comprising
   (i) enriched CD133$^+$/CD34$^+$/CXCR4$^-$ cells isolated from umbilical cord blood; and
   (ii) serum from the subject;
wherein the enriched CD133$^+$/CD34$^+$/CXCR4$^-$ cells are administered by infusion into a coronary artery, and wherein administering of the CD133$^+$/CD34$^+$/CXCR4$^-$ cells results in improved blood flow to said ischemic myocardium.

4. The method of claim 3, wherein the coronary artery is an epicardial vessel that provides collateral flow to said ischemic but viable myocardium in the distribution of a chronic partially or totally occluded vessel.

5. The method of claim 1, wherein the solution further comprises serum from the subject.

6. The method of claim 1, wherein the solution further comprises soluble human fibronectin, hyaluronan or type I collagen, or a combination thereof 7. The method of claim 1, wherein the intracoronary injection comprises injection into an epicardial vessel that provides collateral flow to said ischemic but viable myocardium in the distribution of a chronic partially or totally occluded vessel.

8. The method of claim 1, wherein step (iv) further comprises administering to the subject mesenchymal stem cells isolated from umbilical cord blood.

9. The method of claim 8, wherein administration of the mesenchymal stem cells comprises intracoronary injection of the of the mesenchymal stem cells.

10. The method of claim 8, wherein the mesenchymal stem cells and the CD133+/CD34$^+$/CXCR4$^-$ cells are mixed prior to administration into the subject.

11. The method of claim 1, further comprising administering to the subject a cytokine, chemokine or growth factor.

12. The method of claim 11, wherein the growth factor is bFGF or VEGF.

13. The method of claim 1, further comprising administering to the subject an anticoagulant.

14. The method of claim 1, wherein the CD133+/CD34$^+$/CXCR4$^-$ cells are CD133+CD34+CXCR4–KDR- cells.

15. The method of claim 1, wherein at least 10% of cells in the enriched population are CD133+ cells.

16. The method of claim 1, wherein at least 50% of cells in the enriched population are CD133+ cells.

17. The method of claim 1, wherein at least 75% of cells in the enriched population are CD133+ cells.

18. The method of claim 1, wherein the enriched population of CD133+/CD34$^+$/CXCR4$^-$ cells is not expanded in culture prior to administration into the subject.

19. The method of claim 1, wherein prior to administration the enriched population of CD133+/CD34$^+$/CXCR4$^-$ cells is expanded in vitro under conditions that promote the formation of endothelial cells.

20. The method of claim 19, wherein the conditions that promote the formation of endothelial cells comprise cell culture media comprising
   (a) FBS;
   (b) horse serum;
   (c) hydrocortisone;
   (d) Stem cell growth factor (SCGF);
   (e) VEGF; or
   (f) a combination thereof.

21. The method of claim 1, wherein the therapeutically effective amount of CD133+/CD34$^+$/CXCR4$^-$ cells comprises between $1 \times 10^4$ to $5 \times 10^8$ cells.

22. The method of claim 1, wherein the therapeutically effective amount of the CD133+/CD34$^+$/CXCR4$^-$ cells is a minimum number of cells necessary for increased blood flow induction to the ischemic myocardium.

* * * * *